United States Patent
Knudson et al.

(10) Patent No.: US 7,844,338 B2
(45) Date of Patent: *Nov. 30, 2010

(54) HIGH FREQUENCY OBESITY TREATMENT

(75) Inventors: Mark B. Knudson, Shoreview, MN (US); Richard R. Wilson, Arden Hills, MN (US); Katherine S. Tweden, Mahtomedi, MN (US); Timothy R. Conrad, Eden Prairie, MN (US)

(73) Assignee: EnteroMedics Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/881,045

(22) Filed: Jun. 30, 2004

(65) Prior Publication Data

US 2005/0038484 A1 Feb. 17, 2005

Related U.S. Application Data

(63) Continuation-in-part of application No. 10/674,324, filed on Sep. 29, 2003, now abandoned, and a continuation-in-part of application No. 10/674,330, filed on Sep. 29, 2003, now Pat. No. 7,489,969, and a continuation-in-part of application No. 10/675,818, filed on Sep. 29, 2003, now abandoned, and a continuation-in-part of application No. 10/752,940, filed on Jan. 6, 2004, now Pat. No. 7,444,183, and a continuation-in-part of application No. 10/752,944, filed on Jan. 6, 2004, now Pat. No. 7,167,750, which is a continuation-in-part of application No. 10/358,093, filed on Feb. 3, 2003, now abandoned.

(51) Int. Cl.
*A61N 1/18* (2006.01)

(52) U.S. Cl. ....................................... 607/40

(58) Field of Classification Search ............. 607/40–41, 607/2, 45–46, 133, 149, 48

See application file for complete search history.

(56) References Cited

U.S. PATENT DOCUMENTS 3,128,760 A 4/1964 Baker (Continued)

FOREIGN PATENT DOCUMENTS

EP 0076070 4/1983

(Continued)

OTHER PUBLICATIONS

U.S. Appl. No. 10/674,324, filed Sep. 29, 2003.

(Continued)

*Primary Examiner*—Carl H Layno
*Assistant Examiner*—Jessica Sarcione
(74) *Attorney, Agent, or Firm*—Merchant & Gould P.C.

(57) ABSTRACT

A method for treating at least one of a plurality of disorders characterized at least in part by vagal activity includes positioning an electrode around a body organ innervated by the vagus. An electrical signal is applied to the electrode to modulate vagal activity. The electrical signal is applied at a frequency selected for the signal to create a neural conduction block to the vagus with the neural conduction block selected to at least partially block nerve impulses on the vagus. The application of the electrical signal is discontinued. The application of the signal and the discontinuing of the signal are repeated with durations of the discontinuing and the application selected to treat the disorder.

24 Claims, 8 Drawing Sheets

U.S. PATENT DOCUMENTS

| | | |
|---|---|---|
| 3,411,507 A | 11/1968 | Wingrove |
| 4,114,625 A | 9/1978 | Onat |
| 4,198,963 A | 4/1980 | Barkalow et al. |
| 4,541,432 A | 9/1985 | Molina-Negro et al. |
| 4,702,254 A | 10/1987 | Zabara |
| 4,776,349 A | 10/1988 | Nashef et al. |
| 4,867,164 A | 9/1989 | Zabara |
| 5,025,807 A | 6/1991 | Zabara |
| 5,188,104 A | 2/1993 | Wernicke et al. |
| 5,199,430 A | 4/1993 | Fang et al. |
| 5,215,086 A | 6/1993 | Terry, Jr. et al. |
| 5,226,429 A | 7/1993 | Kuzmak |
| 5,231,988 A | 8/1993 | Wernicke et al. |
| 5,263,480 A | 11/1993 | Wernicke et al. |
| 5,269,303 A | 12/1993 | Wernicke et al. |
| 5,292,344 A | 3/1994 | Douglas |
| 5,299,569 A | 4/1994 | Wernicke et al. |
| 5,330,515 A | 7/1994 | Rutecki et al. |
| 5,335,657 A | 8/1994 | Terry et al. |
| 5,344,438 A | 9/1994 | Testerman |
| 5,370,675 A * | 12/1994 | Edwards et al. ............. 607/101 |
| 5,423,872 A | 6/1995 | Cigaina |
| 5,437,291 A | 8/1995 | Pasricha et al. |
| 5,514,175 A | 5/1996 | Kim et al. |
| 5,540,730 A | 7/1996 | Terry, Jr. et al. |
| 5,571,150 A | 11/1996 | Wernicke et al. |
| 5,601,604 A | 2/1997 | Vincent |
| 5,620,955 A | 4/1997 | Knight et al. |
| 5,690,691 A | 11/1997 | Chen et al. |
| 5,707,400 A | 1/1998 | Terry, Jr. et al. |
| 5,716,385 A | 2/1998 | Mittal et al. |
| 5,747,060 A | 5/1998 | Sackler et al. |
| 5,749,907 A | 5/1998 | Mann |
| 5,830,434 A * | 11/1998 | Taylor et al. ................ 424/9.2 |
| 5,836,994 A | 11/1998 | Bourgeois |
| 5,861,014 A | 1/1999 | Familoni |
| 5,919,216 A | 7/1999 | Houben et al. |
| 5,967,977 A | 10/1999 | Mullis et al. |
| 5,995,872 A | 11/1999 | Bourgeois |
| 6,083,249 A | 7/2000 | Familoni |
| 6,091,992 A | 7/2000 | Bourgeois et al. |
| 6,093,167 A | 7/2000 | Houben et al. |
| 6,097,984 A | 8/2000 | Douglas |
| 6,098,629 A | 8/2000 | Johnson et al. |
| 6,104,955 A | 8/2000 | Bourgeois |
| 6,111,715 A | 8/2000 | Tsuchiya et al. |
| 6,129,726 A * | 10/2000 | Edwards et al. .............. 606/41 |
| 6,135,978 A | 10/2000 | Houben et al. |
| 6,148,222 A | 11/2000 | Ramsey, III |
| 6,216,039 B1 | 4/2001 | Bourgeois |
| 6,238,423 B1 | 5/2001 | Bardy |
| 6,243,607 B1 | 6/2001 | Mintchev et al. |
| 6,261,280 B1 | 7/2001 | Houben et al. |
| 6,261,572 B1 | 7/2001 | Donovan |
| 6,290,961 B1 | 9/2001 | Aoki et al. |
| 6,292,703 B1 | 9/2001 | Meier et al. |
| 6,308,105 B1 | 10/2001 | Duysens et al. |
| 6,312,708 B1 | 11/2001 | Donovan |
| 6,341,236 B1 | 1/2002 | Osorio et al. |
| 6,364,899 B1 | 4/2002 | Dobak, III |
| 6,369,079 B1 | 4/2002 | Rubin et al. |
| 6,405,732 B1 | 6/2002 | Edwards et al. |
| 6,418,346 B1 | 7/2002 | Nelson et al. |
| 6,449,511 B1 | 9/2002 | Mintchev et al. |
| 6,473,644 B1 | 10/2002 | Terry, Jr. et al. |
| 6,532,388 B1 | 3/2003 | Hill et al. |
| 6,558,708 B1 | 5/2003 | Lin |
| 6,571,127 B1 | 5/2003 | Ben-Haim et al. |
| 6,587,719 B1 | 7/2003 | Barrett et al. |
| 6,591,137 B1 | 7/2003 | Fischell |
| 6,609,025 B2 | 8/2003 | Barrett et al. |
| 6,610,713 B2 | 8/2003 | Tracey |
| 6,611,715 B1 | 8/2003 | Boveja |
| 6,612,983 B1 * | 9/2003 | Marchal ...................... 600/300 |
| 6,622,038 B2 | 9/2003 | Barrett et al. |
| 6,684,105 B2 | 1/2004 | Cohen et al. |
| 6,746,474 B2 | 6/2004 | Saadat |
| 6,826,428 B1 | 11/2004 | Chen et al. |
| 6,832,114 B1 | 12/2004 | Whitehurst et al. |
| 6,853,862 B1 * | 2/2005 | Marchal et al. ............... 607/40 |
| 6,895,278 B1 | 5/2005 | Gordon |
| 6,928,320 B2 | 8/2005 | King |
| 6,993,391 B2 | 1/2006 | Flesler et al. |
| 7,054,690 B2 | 5/2006 | Imran |
| 7,072,720 B2 | 7/2006 | Puskas |
| 7,076,307 B2 | 7/2006 | Boveja et al. |
| 7,142,910 B2 | 11/2006 | Puskas |
| 7,167,750 B2 | 1/2007 | Knudson et al. |
| 7,292,890 B2 | 11/2007 | Whitehurst et al. |
| 7,299,091 B2 | 11/2007 | Barrett |
| 7,340,306 B2 | 3/2008 | Barrett |
| 7,444,183 B2 | 10/2008 | Knudson |
| 7,444,184 B2 | 10/2008 | Boveja |
| 7,489,969 B2 | 2/2009 | Knudson et al. |
| 7,613,515 B2 | 11/2009 | Knudson et al. |
| 7,620,455 B2 | 11/2009 | Maschino |
| 7,630,769 B2 | 12/2009 | Knudson |
| 7,693,577 B2 | 4/2010 | Knudson |
| 7,720,540 B2 | 5/2010 | Knudson |
| 7,729,771 B2 | 6/2010 | Knudson |
| 2001/0012828 A1 | 8/2001 | Aoki et al. |
| 2001/0051787 A1 | 12/2001 | Haller et al. |
| 2002/0032468 A1 | 3/2002 | Hill et al. |
| 2002/0052336 A1 | 5/2002 | Yerxa et al. |
| 2002/0055779 A1 | 5/2002 | Andrews |
| 2002/0072780 A1 | 6/2002 | Foley |
| 2002/0087192 A1 | 7/2002 | Barrett et al. |
| 2002/0094962 A1 | 7/2002 | Ashley et al. |
| 2002/0103424 A1 | 8/2002 | Swoyer et al. |
| 2002/0161360 A1 * | 10/2002 | Carroll ....................... 606/21 |
| 2002/0198570 A1 | 12/2002 | Puskas |
| 2002/0198571 A1 | 12/2002 | Puskas |
| 2003/0014086 A1 | 1/2003 | Sharma |
| 2003/0018367 A1 | 1/2003 | DiLorenzo |
| 2003/0040785 A1 | 2/2003 | Maschino et al. |
| 2003/0045909 A1 | 3/2003 | Gross et al. |
| 2003/0045914 A1 * | 3/2003 | Cohen et al. .................. 607/62 |
| 2003/0074039 A1 | 4/2003 | Puskas |
| 2003/0135248 A1 | 7/2003 | Stypulkowski |
| 2003/0144709 A1 | 7/2003 | Zabara et al. |
| 2003/0171789 A1 | 9/2003 | Malek et al. |
| 2003/0181958 A1 | 9/2003 | Dobak, III |
| 2003/0181959 A1 | 9/2003 | Dobak, III |
| 2003/0195601 A1 | 10/2003 | Hung et al. |
| 2003/0212440 A1 | 11/2003 | Boveja |
| 2004/0039425 A1 | 2/2004 | Greenwood-Van Meerveld |
| 2004/0059383 A1 | 3/2004 | Puskas |
| 2004/0086531 A1 | 5/2004 | Barron |
| 2004/0089313 A1 | 5/2004 | Utley et al. |
| 2004/0127953 A1 | 7/2004 | Kilgore et al. |
| 2004/0167583 A1 * | 8/2004 | Knudson et al. .............. 607/40 |
| 2004/0172084 A1 | 9/2004 | Knudson et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0176812 A1 | 9/2004 | Knudson et al. |
| 2004/0181178 A1 | 9/2004 | Aldrich et al. |
| 2004/0193229 A1 | 9/2004 | Starkebaum et al. |
| 2004/0236381 A1 | 11/2004 | Dinsmoor et al. |
| 2004/0236382 A1 | 11/2004 | Dinsmoor et al. |
| 2004/0243182 A1 | 12/2004 | Cohen et al. |
| 2004/0249416 A1 | 12/2004 | Yun et al. |
| 2004/0254616 A1 | 12/2004 | Rossing et al. |
| 2005/0038484 A1 | 2/2005 | Knudson et al. |

| | | | |
|---|---|---|---|
| 2005/0049655 A1 | 3/2005 | Boveja et al. | |
| 2005/0070970 A1 | 3/2005 | Knudson et al. | |
| 2005/0070974 A1 | 3/2005 | Knudson et al. | |
| 2005/0075693 A1 | 4/2005 | Toy et al. | |
| 2005/0131485 A1 | 6/2005 | Knudson et al. | |
| 2005/0137644 A1 | 6/2005 | Boveja et al. | |
| 2005/0143378 A1 | 6/2005 | Yun et al. | |
| 2005/0143412 A1 | 6/2005 | Puskas | |
| 2005/0143787 A1 | 6/2005 | Boveja et al. | |
| 2005/0149141 A1 | 7/2005 | Starkebaum | |
| 2005/0149146 A1 | 7/2005 | Boveja et al. | |
| 2005/0149148 A1 | 7/2005 | King | |
| 2005/0203501 A1 | 9/2005 | Aldrich et al. | |
| 2005/0240231 A1 | 10/2005 | Aldrich et al. | |
| 2005/0267542 A1 | 12/2005 | David | |
| 2006/0015151 A1 | 1/2006 | Aldrich | |
| 2006/0030919 A1 | 2/2006 | Mrva et al. | |
| 2006/0036293 A1 | 2/2006 | Whitehurst et al. | |
| 2006/0041277 A1 | 2/2006 | Deem | |
| 2006/0190053 A1 | 8/2006 | Dobak, III | |
| 2006/0212089 A1 | 9/2006 | Tass et al. | |
| 2006/0229685 A1 | 10/2006 | Knudson et al. | |
| 2006/0247737 A1 | 11/2006 | Olson | |
| 2007/0027484 A1 | 2/2007 | Guzman et al. | |
| 2007/0043400 A1 | 2/2007 | Donders et al. | |
| 2007/0135846 A1 | 6/2007 | Knudson et al. | |
| 2007/0135856 A1 | 6/2007 | Knudson et al. | |
| 2007/0135857 A1 | 6/2007 | Knudson et al. | |
| 2007/0135858 A1 | 6/2007 | Knudson et al. | |
| 2007/0142870 A1 | 6/2007 | Knudson et al. | |
| 2008/0021512 A1 | 1/2008 | Knudson et al. | |

FOREIGN PATENT DOCUMENTS

| | | |
|---|---|---|
| EP | 1 666 087 A1 | 2/1998 |
| EP | 0 865 800 A2 | 9/1998 |
| EP | 0 896 828 A2 | 2/1999 |
| EP | 1 004 330 A1 | 5/2000 |
| WO | WO 01/41671 A2 | 6/2001 |
| WO | WO 01/43821 A1 | 6/2001 |
| WO | WO 02/26320 A1 | 4/2002 |
| WO | WO-02/065896 A2 * | 8/2002 |
| WO | WO 2004/036377 A2 | 4/2004 |
| WO | WO 2004/064918 A1 | 8/2004 |
| WO | WO 2004/082763 A1 | 9/2004 |
| WO | WO 2004/110551 A2 | 12/2004 |

OTHER PUBLICATIONS

U.S. Appl. No. 10/674,330, filed Sep. 29, 2003.
U.S. Appl. No. 10/675,818, filed Sep. 29, 2003.
U.S. Appl. No. 10/752,940, filed Jan. 6, 2004.
U.S. Appl. No. 10/752,944, filed Jan. 6, 2004.
U.S. Appl. No. 10/756,166, filed Jan. 12, 2004.
U.S. Appl. No. 10/756,176, filed Jan. 12, 2004.
Kilgore, K. et al., "Nerve Conduction Block Utilising High-Frequency Alternating Current," *Medical & Biological Engineering & Computing*, vol. 42, pp. 394-406 (2004).
Product Brochure, "ATROSTIM Phrenic Nerve Stimulator," AtroTech Oy, P.O. Box 28, FIN-33721 Tampere, Finland, 2 pages (Jun. 2004).
Accarino, et al, "Symptomatic Responses To Stimulation Of Sensory Pathways In The Jejunum", *Am. J. Physiol.*, vol. 263, pp. G673-G677 (1992).
Accarino, et al, "Selective Dysfunction Of Mechano Sensitive Intestinal Afferents In Irritable Bowel Syndrome", *Gastroenterology*, vol. 108, pp. 636-643 (1994).
Accarino, et al, "Attention And Distraction Colon Affects On Gut Perception", *Gastroenterology*, vol. 113, pp. 415-442 (1997).
Accarino, et al "Modification Of Small Bowel Mechanosensitivity By Intestinal Fat", *GUT*, vol. 48, pp. 690-695 (2001).
Accarino, et al, "Gut Perception In Humans Is Modulated By Interacting Gut Stimuli", *Am. J. Physiol. Gastrointestinal Liver Physiol.*, vol. 282, pp. G220-G225 (2002).

U.S. Appl. No. 10/674,330, Aggarwal A, et al., "Predominant Symptoms in Irritable Bowel Syndrome Correlate with Specific Autonomic Nervous system Abnormalities", *Gastroenterol*, (1994);106:945-950.
U.S. Appl. No. 10/674,330, Amaris et al., "Microprocessor controlled movement of solid colonic content using sequential neural electrical stimulation", *Gut*, 50: pp. 475-479 (2002).
Bard® Minnesota Four Lumen Esophagogastric Tamponade Tube for the Control of Bleeding from Esophageal Varices (Instructions for Use), C. R. Bard, Inc., Covington, GA, USA (1998).
Baron, et al., "Acute Necrotizing Pancreatitis", *New England J. of Medicine*, vol. 340, No. 18, pp. 1412-1417 (1999).
U.S. Appl. No. 10/674,330, Batterham, et al., "Inhibition of Food Intake in Obese Subjects by Peptide YY3-36", *New England J. Med.*, pp. 941-948 (Sep. 4, 2003).
U.S. Appl. No. 10/358,093, Beglinger et al., "Postprandial Control of Gallbladder Contraction and Exocrine Pancreatic Secretion in Man", Euro. J. of Clinical Investigation, pp. 827-834 (1992).
U.S. Appl. No. 10/358,093, Bell, et al., "The Interplay between Hydrogen Ions, Bicarbonate Ions and Osmolality in the Anterior Duodenuym Modulating Gastric Fuction in the Conscious Calf", *J. Physiol.*, pp. 331-341 (1981).
U.S. Appl. No. 10/358,093, Benini, "Gastric Emptying and Dyspeptic Symptoms in Patients with Gastroesophageal Reflux", Amer. J. of Gastroenterology, pp. 1351-1354 (1996).
U.S. Appl. No. 10/358,093, Benini, et al., "Omeprazole Causes Delay in Gastric Emptying of Digestible Meals", *Digestive Diseases and Sciences*, pp. 469-474 (1996).
U.S. Appl. No. 10/358,093, Berthoud et al., "Characteristics of Gastric and Pancreatic Responses to Vagal Stimulation with Varied Frequencies: Evidence for Different Fiber Calibers?", *J. Auto. Nervous Sys.*, pp. 77-84 (1987).
Biron, et al., "Clinical Experience with Biliopancreatic Bypass and Gastrectomy or Selective Vagotomy for Morbid Obesity", *Canadian J. of Surg.*, vol. 29, No. 6, pp. 408-410 (1986).
U.S. Appl. No. 10/358,093, Bourde, et al., "Vagal Stimulation: II. Its Effect on Pancreatic Secretion in Conscious Dogs", *Annals of Surgery*, pp. 357-364 (1970).
"Bravo™ pH Monitoring System Catheter-Free pH Testing", document No. UC 200300235 EN N15344, Medtronic, Inc., Minneapolis, Minnesota, USA (2002).
Burneo, et al., "Weight Loss Associated With Vagus Nerve Stimulation", *Neurology*, vol. 59, pp. 463-464 (Aug. (1 of 2) 2002).
U.S. Appl. No. 10/674,330, Cann PA, et al. "Irritable Bowel Syndrome: Relationship of Disorders in the Transit of a Single Solid Meal to Symptoms Patterns", *Gut*, (1983);24:405-411.
Chatzicostas, et al., "Balthazar computed tomography severity index is superior to Ranson criteria and APACHE II and II scoring systems in predicting acute pancreatitis outcome", *J. Clinical Gastroenterology*, 36(3), pp. 253-260 (2003).
U.S. Appl. No. 10/358,093, Chey et al., "Neural Hormonal Regulation of Exocrine Pancreatic Secretion", Pancreatology, pp. 320-335 (2001).
U.S. Appl. 10/358,093, Chey, "Regulation of Pancreatic Exocrine Secretion", Int'l J. of Pancreatology, pp. 7-20 (1991).
Cigaina, "Gastric Pacing As Therapy For Morbid Obesity", *Obesity Surgery*, vol. 12, Supplement, pp. 12S-16S (2002).
Coffin, et al, "Somatic Stimulation Reduces Perception Of Gut Distention In Humans", *Gastroenterology*, vol. 107, pp. 1636-1642 (1994).
U.S. Appl. No. 10/674,330, Cuomo R, et al., "Functional Dyspepsia Symptoms, Gastric Emptying and Satiety Provocation Test: Analysis of Relationships", *Scand J Gastroenterol*, (2001) 36:1030-1036.
Cyberonics, Inc 2001 Annual Report, pp. 1, 5-7 and 16 (2001).
Cyberonics, Inc. 2003 Form 10-K to Securities and Exchange Commission, pp. 1 and 10 as printed on May 23, 2006 from http://www.secinfo.com/dsvRu.23yb.htm.
D'Argent, "Gastric Electrical Stimulation: Preliminary Results", *Obesity Surgery*, vol. 12, Supplement, pp. 21S-25S (2002).
U.S. Appl. No. 10/674,330, Dapoigny et al., "Vagal influence on colonic motor activity in conscious nonhuman primates", *Am. J. Physiol.*, 262: G231-G236 (1992).

U.S. Appl. No. 10/674,330, DeVault KR, et al., "Updated Guidelines for the Diagnosis and Treatment of Gastroesophageal Reflux Disease", *Am J Gastroenterol*, (1999);94:1434-1442.

U.S. Appl. No. 10/674,330, Drossman, "Rome II: A Multinational Consensus Document on Gastrointestinal Disorders—The Functional Gastrointestinal Disorders and the Rome II Process", *Gut*, vol. 45 (Suppl II):111-115 (1999).

U.S. Appl. No. 10/358,093, Estcvão-Costa et al., "Delayed Gastric Emptying and Gastroesophageal Reflux: A Pathophysiologic Relationship", J. of Pediatric Gastroenterology and Nutrition, pp. 471-474 (2001).

U.S. Appl. No. 10/674,330, Evans PR, et al., "Gastroparesis and Small Bowel Dysmotility in Irritable Bowel Syndrome", *Dig Dis Sci* (1997);42:2087-2093.

U.S. Appl. No. 10/674,330, Evans PR, et al., "Jejunal Sensorimotor Dysfunction in Irritable Bowel Syndrome: Clinical and Psychosocial Features", Gastroenterol, (1996);110:393-404.

Faris, et al., "Effect of Decreasing Afferent Vagal Activity with Ondansetron on Symptoms of Bulimia Nervosa: a Randomized, Double-Blind Trial", *The Lancet*, pp. 792-797 (2000).

George, et al., "Vagus Nerve Stimulation Therapy", *Neurology*, vol. 59 (Supp) 4) pp. S56-S61 (2002).

U.S. Appl. No. 10/674,330, Gershon, "The Second Brain", Harper Collins Publishers, Inc, New York, NY p. 19 (1998).

Gortz, et al., "Truncal Vagotomy Reduces Food and Liquid Intake in Man", *Physiology & Behavior*, vol. 48, pp. 779-781 (1990).

Gray, *Anatomy of the Human Body*, 13$^{th}$ Ed., C. Clemente, Editor, (Lea & Febiger, Philadelphia, PA USA, Publisher) (1985) title pages and p. 69, 70 and 1186.

U.S. Appl. No. 10/358,093, Grossi, et al., "Swallows, Oesophageal and Gastric Motility in Normal Subjects and in Patients with Gastro-Oesophageal Reflux Disease: a 24-H pH-Manometric Study", Neurogastroenterology and Motility, pp. 115-121 (1998).

U.S. Appl. No. 10/674,330, Guyton AC, et al., "Propulsion and Mixing of Food in the Alimentary Tract", Textbook of Medical Physiology, 10$^{th}$ ed. Philadelphia: W. B. Saunders and Company, 200:728-737.

U.S. Appl. No. 10/674,330, Guyton AC, et al., "Secretory Functions of the Alimentary Tract", Textbook of Medical Physiology, 10$^{th}$ ed. Philadelphia: W. B. Saunders and Company, 200:738-753.

U.S. Appl. No. 10/674,330, Hausken, et al., "Low Vagal Tone and Antral Dysmotility in Patients with Functional Dyspepsia", *Psychosomatic Medicine*, 55: 12-22 (1993).

U.S. Appl. No. 10/674,330, Heitkemper, et al., "Evidence for Automatic Nervous System Imbalance in Women with Irritable Bowel Syndrome", *Digestive Diseases and* Sciences, vol. 43, No. 9, pp. 2093-2098 (1998).

U.S. Appl. No. 10/674,330, Hjelland, et al., "Vagal tone and meal-induced abdominal symptoms in healthy subjects", Digestion, 65: 172-176 (2002).

U.S. Appl. No. 10/674,330, Holst et al "Nervous control of pancreatic endocrine secretion in pigs" *Acta Physiol Scand*, (1981), 111:1-7.

Holst et al., "Nervous Control of Pancreatic Exocrine Secretion in Pigs", *Acta Physiol. Scand.*, vol. 105, pp. 33-51 (1979).

U.S. Appl. No. 10/674,330, Hornbuckle K, et al. "The Diagnosis and Work-Up of the Patient with Gastroparesis", *J Clin Gastroenterol*, (2000);30:117-124.

U.S. Appl. No. 10/358,093, Hunt, "The Relationship Between The Control Of pH And Healing And Symptom Relief In Gastro-Oesophageal Reflux Disease", *Ailment Pharmacol Ther.*, 9 (Suppl. 1) pp. 3-7 (1995).

ICD-10, "Classification of Mental and Behavioural Disorders", World Health Organization (1992), 2 pages, printed from http://www.mental-health-matters.com/disorders/dis_details.

Kaiser, "Gallstone Ileus", *New England J. of Medicine*, vol. 336, No. 12, pp. 879-880 (1997) (correspondence).

U.S. Appl. No. 10/358,093, Kaminski et al., "The Effect of Electrical Vagal Stimulation on Canine Pancreatic Exocrine Function", Surgery, pp. 545-552 (1975).

U.S. Appl. No. 10/674,330, Kellow JE, et al., "Dysmotility of the Small Intestine in Irritable Bowel Syndrome", *Gut*, (1988);29:1236-1243.

U.S. Appl. No. 10/674,330, Kellow JE, et al., "Rome II: A Multinational Consensus Document on Gastrointestinal Disorders—Principles of Applied Neurogastroenterology: Physiology/Motility-Sensation", *Gut*, (1999);45(Suppl II):1117-1124.

Koren et al., "Vagus Nerve Stimulation Does Not Lead To Significant Changes In Body Weight In Patients With Epilepsy", *Epilepsy & Behavior*, vol. 8, pp. 246-249 (2005).

U.S. Appl. No. 10/674,330, Korner et al., "To Eat or Not to Eat—How the Gut Talks to the Brain", *New England J. Med.*, pp. 926-928 (Sep. 4, 2003).

Kosel, et al., "Beyond the Treatment of Epilepsy: New Applications of Vagus Nerve Stimulation in Psychiatry", *CNS Spectrums*, vol. 8, No. 7, pp. 515-521 (Jul. 2003).

Kral, "Vagotomy for Treatment of Severe Obesity", *The Lancet*, pp. 307-308 (1978).

Kral, "Vagotomy as a Treatment for Morbid Obesity", *Surg. Clinics of N. Amer.*, vol. 59, No. 6, pp. 1131-1138 (1979).

Kral, et al., "Gastroplasty for Obesity: Long--Term Weight Loss Improved by Vagotomy", *World J. Surg.*, vol. 17, pp. 75-79 (1993).

U.S. Appl. No. 10/674,330, Lagergren J, et al., "Symptomatic Gastroesophageal Reflux as a Risk Factor for Esophageal Adenocarcinoma", *New Engl J Med*, (1999);340:825-831.

U.S. Appl. No. 10/674,330, Lin et al., "Hardware—software co-design of portable functional gastrointestinal stimulator system", *J. of Medical Eng. & Tech.*, vol. 27, No. 4 pp. 164-177 (2003).

U.S. Appl. No. 10/358,093, Long, M.S. editor, Chapter 3, "The Stomach", Gastrointestinal System, 2$^{nd}$ Ed., Mosby Publisher, London (2002).

U.S. Appl. No. 10/358,093, Long, M.S. editor, Chapter 4, "The Liver and Biliary Tract", Gastrointestinal System, 2$^{nd}$ Ed., Mosby Publisher, London (2002).

U.S. Appl. No. 10/358,093, Mabayo, et al., "Inhibition of Food Passage by Osmeprazole in the Chicken", European J. of Pharmacology, pp. 161-165 (1995).

Martin-Portugues, et al., "Histopathologic Features of the Vagus Nerve After Electrical Stimulation in Swine", *Histol Histopathol*, vol. 20, pp. 851-856 (2005).

"Medical Care for Obese Patients", U.S. Department of Health and Human Services, National Institute of Diabetes and Digestive and Kidney Diseases, pp. 1-6, NIH Publication No. 03-5335, Feb. 2003.

Medical Encyclopedia: Anorexia Nervosa, U.S. National Library of Medicine and National Institutes of Health, pp. 1-3 (Jun. 22, 2004) printed from http://www.nlm.nih.gov/medlineplus/print/ency/article/000362.htm, Jun. 6, 2006.

U.S. Appl. No. 10/674,330, Merio R, et al., "Slow Gastric Emptying in Type I Diabetes: Relation to Autonomic and Peripheral Neuropathy, Blood Glucose, and Glycemic Control", *Diabetes Care*, (1997);20:419-423.

U.S. Appl. No. 10/674,330, Mintchev, et al., "Electrogastrographic impact of multi-site functional gastric electrical stimulation", *J. of Medical Eng. & Tech.*, vol. 23, No. 1 pp. 5-9 (1999).

U.S. Appl. No. 10/674,330, Mittal RK, et al., "Mechanism of Disease: The Esophagogastric Junction", *New Engl J Med*, (1997);336:924-932.

Netter, "Atlas of Human Anatomy", 3rd Ed., Plate 120, (Icon Learning Systems, New Jersey) (2003).

Norton, et al., "Optimizing Outcomes in Acute Pancreatitis", *Drugs*, 61(11), pp. 1581-1591 (2001).

U.S. Appl. 10/674,330, Novartis product description, Zelnorm®, Jul. 2002 (T2002-19).

O'Brien, P. et al., "The Laparoscopic Adjustable Gastric Band (Lap-Band®): A Prospective Study of Medium-Term Effects on Weight, Health and Quality of Life," *Obesity Surgery*, vol. 12, pp. 652-660 (2002).

"Obesity and Technology: Can the stomach be fooled", Reuters (Apr. 26, 2006), 3 pages, http://news.yahoo.com/s/nm/20060426/us_nm/bizfeature_obesity_technology_de&printer as printed on May 23, 2006.

U.S. Appl. No. 10/358,093, Owyang, "Negative Feedback Control of Exocrine Pancrfeatic Secretion: Role of Cholecystokinin and Cholinergic Pathway", Symposium: Physiology of Cholecystokinin, American Institute of Nutrition, pp. 1321S-1326S (1994).

U.S. Appl. No. 10/674,330, Paterson CA, et al., "Determinants of Occurrence and Volume of Transpyloric Flow During Gastric Emptying of Liquids in Dogs: Importance of Vagal Input", *Dig Dis Sci*, (2000);45:1509-1516.

Peeters, et al., "Obesity in Adulthood and Its Consequences for Life Expectancy: A Life Table Analysis", *Annals of Internal Medicine*, vol. 138, No. 1, pp. 24-32 (2003).

U.S. Appl. No. 10/674,330, Petrofsky, et al., "Impact of Recruitment Order on Electrode Design for Neural Prosthetics of Skeletal Muscle", *Am. J. of Physical Medicine*, vol. 60, No. 5, pp. 243-253 (1981).

U.S. Appl. No. 10/674,330, Poelmans J, et al., "Prospective Study on the Incidence of Chronic Ear Complaints Related to Gastroesophageal Reflux and on the Outcome of Antireflux Therapy", *Ann Otol Rhinol Laryngol*, (2002);111:933-938.

U.S. Appl. No. 10/674,330, Rashev et al., "Microprocessor-Controlled Colonic Peristalsis", *Digestive Diseases and Sciences*, vol. 47, No. 5, pp. 1034-1048 (2002).

U.S. Appl. No. 10/674,330, Rashev, et al., "Three-dimensional static parametric modeling of phasic colonic contractions for the purpose of microprocessor-controlled functional stimulation", *J. of Medical Eng. & Tech.*, vol. 25, No. 3 pp. 85-96 (2001).

U.S. Appl. No. 10/358,093, Rasmussen, et al., "A Double-Blind Placebo-Controlled Study on the Effects of Omeprazole on Gut Hormone Secretion and Gastric Emptying Rate", Scand. J. Gastroenterol, pp. 900-905 (1997).

U.S. Appl. No. 10/358,093, Rösch et al., "Frequency-Dependent Secretion of Pancreatic Amylase, Lipase, Trypsin, and Chymotrypsin During Vagal Stimulation in Rats", *Pancreas*, pp. 499-506 (1990).

Roslin, et al., "Vagus Nerve Stimulation in the Treatment of Morbid Obesity", Ch. 6 to *Vagus Nerve Stimulation*, $2^{nd}$ Ed., pp. 113-121 (Schlachter et al. ed., Martin Dunitz), 2003.

Roslin et al., "The Use Of Electrical Stimulation Of The Vagus Nerve To Treat Morbid Obesity", *Epilepsy & Behavior*, vol. 2, S11-S16 (2001) at p. S13.

U.S. Appl. No. 10/674,330, Sarnelli G, et al., "Symptoms Associated with Impaired Gastric Emptying of Solids and Liquids in Functional Dyspepsia", *Am J Gastroenterol*, (2003) 98:783-788.

U.S. Appl. No. 10/674,330, Scheffer RC, et al., "Elicitation of Transient Lower Oesophageal Sphincter Relaxations in Response to Gastric Distension", *Neurogastroenterol Motil*, (2002);14:647-655.

U.S. Appl. No. 10/358,093, Schapiro, et al., "Neurohypophyseal Regulation of the Exocrine Pancreas", *Amer. J. of Gastroenterolgy*, pp. 587-591 (1979).

U.S. Appl. No. 10/674,330, Schmidt T, et al., "Ambulatory 24-Hour Jejunal Motility in Diarrhea-Predominant Irritable Bowel Syndrome", *J Gastroenterol*, (1996);31:581-589.

U.S. Appl. No. 10/674,330, Schwartz MP, et al., "Chemospecific Alterations in Duodenal Perception and Motor Response in Functional Dyspepsia", *Am J Gastroenterol*, (2001);96:2596-2602.

U.S. Appl. No. 10/674,330, Schwartz MP, et al., "Human Duodenal Motor Activity in Response to Acid and Different Nutrients", *Dig Dis Sci*, (2001);46:1472-1481.

Shikora, "'What are the Yanks Doing' The U.S. Experience with Implantable Gastric Stimulation (IGS) for the Treatment of Obesity—Update on the Ongoing Clinical Trials", *Obesity Surgery*, vol. 14, Supplement, S40-S48 (2004).

U.S. Appl. No. 10/674,330, Simren M, et al., "Abnormal Propagation Pattern of Duodenal Pressure Waves in the Irritable Bowel Syndrome (IBS)", *Dig Dis Sci*, (2000);45:2151-2161.

Smith, et al., "Truncal Vagotomy in Hypothalamic Obesity", *The Lancet*, pp. 1330-1331 (1983).

U.S. Appl. No. 10/674,330, Solomonow, et al., "Control of Muscle Contractile Force through Indirect High-Frequency Stimulation", *Am. J. of Physical Medicine*, vol. 62, No. 2, pp. 71-82 (1983).

U.S. Appl. No. 10/674,330, Sontag SJ, et al., "Asthmatics with Gastroesophageal Reflux: Long Term Results of a Randomized Trial of Medical and Surgical Antireflux Therapies", *Am J Gastroenterol*, (2003);98:987-999.

Soran, et al., "Outcome and quality of life of patients with acute pancreatitis requiring intensive care", *J. Surg. Res.*, 91(1), pp. 89-94 (2000).

U.S. Appl. No. 10/674,330, Stanghellini V, et al., "Risk Indicators of Delayed Gastric Emptying of Solids in Patients with Functional Dyspepsia", *Gastroenterol*, (1996) 110:1036-1042.

Steer et al., "Chronic Pancreatitis", *New England J. of Medicine*, pp. 1482-1490 (1995).

Steinbrook, R., "Surgery for Severe Obesity", *New England J. Med.*, vol. 350, pp. 1075-1079 (2004).

Steinbrook, "An Opioid Antagonist For Postoperative Ileus", *New England J. of Medicine*, vol. 345, No. 13, pp. 988-989 (2001) (Editorial).

U.S. Appl. No. 10/674,330, Tack J, et al., "Role of Impaired Gastric Accommodation to a Meal in Functional Dyspepsia", *Gastroenterol*, (1998) 115:1346-1352.

U.S. Appl. No. 10/674,330, Tack J, et al., "Symptom Pattern and Gastric Emptying Rate Assessed by the Octanoic Acid Breath Test in Functional Dyspepsia" [abstract]. *Gastroenterol*, (1998) 1.14:A301.

Taguchi, et al., "Selective Postoperative Inhibition of Gastrointestinal Opioid Receptors", *New England J. of Medicine*, vol. 345, No. 13, pp. 935-940 (2001).

U.S. Appl. No. 10/674,330, Talley et al., "Rome II: A Multinational Consensus Document on Gastrointestinal Disorders—Functional Gastroduodenal Disorders" *Gut*, vol. 45 (Suppl II), pp. 137-1142 (1999).

U.S. Appl. No. 10/674,330, Thompson WG, et al., "Rome II: A Multinational Consensus Document on Gastrointestinal Disorders—Functional Bowel Disorders and Functional Abdominal Pain", *Gut*, (1999) ;45(Suppl II):II43-II47.

U.S. Appl. No. 10/358,093, Tiscomia et al., "Neural Control of the Exocrine Pancreas: An Analysis of the Cholinergic, Adrenergic, and Peptidergic Pathways and Their Positive and Negative Components 1: Neural Mechanisms", *Mount Sinai J. of Medicine*, pp. 336-383 (1987).

U.S. Appl. No. 10/674,330, Tougas, "The Autonomic Nervous System in Functional Bowel Disorders", *Gut*, vol. 47 (Suppl IV), pp. iv78-iv80 (2000).

Tzu-Ming, et al., "Long-Term Results of Duodenectomy with Highly Selective Vagotomy in the Treatment of complicated Duodenal Ulcers", *Amer. J. of Surg.*, vol. 181, pp. 372-376 (2001).

U.S. Appl. No. 10/674,330, Undeland KA, et al., "Wide Gastric Antrum and Low Vagal Tone in Patients with Diabetes Mellitus Type I Compared to Patients with Functional Dyspepsia and Healthy Individuals", *Dig Dis Sci*, (1996) 41:9-16.

U.S. Appl. No. 10/674,330, Van Den Honert, et al., "Generation of Unidirectionally Propagated Action Potentials in a Peripheral Nerve by Brief Stimuli", *Science*, vol. 206, pp. 1311-1312.

U.S. Appl. No. 10/674,330, Van Wijk HJ, et al., "Gastric Emptying and Dyspeptic Symptoms in the Irritable Bowel Syndrome", *Scand J Gastroenterol*, (1992);27:99-102.

U.S. Appl. No. 10/674,330, Vassallo MJ, et al., "Colonic Tone and Motility in Patents with Irritable Bowel Syndrome", *Mayo Clin Proc*, (1992);67:725-731.

U.S. Appl. No. 10/674,330, Wilmer A, et al., "Ambulatory Gastrojejunal Manomery in Severe Motility-like Dyspepsia: Lack of Correlation between Dysmotility, Sympotoms and Gastric Emptying", *Gut*, (1998) 42:235-242.

Yoshinaga, et al., "Cholecystokinin Acts as an Essential Factor in the Exacerbation of Pancreatic Bile Duct Ligation-Induced Rat Pancreatitis Model Under Non-Fasting Condition", *Japanese J. Pharmacol*, vol. 84, pp. 44-50 (2000).

Zapater, et al., "Do Muscarinic Receptors Play a Role in Acute Pancreatitis?", *Clin. Drug Invest.*, 20(6), pp. 401-408 (2000).

*Illustrated Stedman's Medical Dictionary*, 24th Edition, Williams & Wilkins, Baltimore, MD, USA, Publisher, title pages and pp. 3 and 1187 (1982).

Balaji, et al., "A Safe and Noninvasive Test for Vagal Integrity Revisited", *Archive Surgery*, vol. 137, pp. 954-959 (2002).

Boss, et al., Laparoscopic Truncal Vagotomy for Severe Obesity: Six Month Experience in 10 Patients from a Prospective, Two-Center Study, Proceedings of the $24^{th}$ Annual Meeting, American Society for Metabolic & Bariatric Surgery, Plenary Session Abstracts, (Abstract No. 44) (Jun. 2007) (reprinted from http://www.asbs.org/archive/abstracts/plenary_edited_2007.pdf).

Camilleri et al., "Determinants of Response to a Prokinetic Agent in Neuropathic Chronic Intestinal Motility Disorder", *American Gastroenterological Association*, vol. 106, No. 4, pp. 916-923 (1994).

Gleysteen, et al., "Reversible Truncal Vagotomy in Conscious Dogs", *Gastroenterology*, vol. 85, pp. 578-583 (1983).

Görtz, et al., "A Five- to Eight-Year Follow-up Study of Truncal Vagotomy as a Treatment for Morbid Obesity", Proceedings of the Third Annual Meeting, American Society for Bariatric Surgery, p. 145 (1986) (Abstract) cited in Applicants' IDS accompanying this Amendment.

Greydanus et al., "Neurohormonal Factors in Functional Dyspepsia: Insights on Pathophysiological Mechanisms", *American Gastroenterological Association*, vol. 100, No. 5 pp. 1311-1318 (1991).

Gui et al., "Botulinum Toxin Injected in the Gastric Wall Reduces Body Weight and Foot Intake in Rats", *Alimentary Pharmacology & Therapeutics*, vol. 14, pp. 829-834 (2000).

Koch et al., "Can Plasma Human Pancreatic Polypeptide Be Used To Detect Diseases of the Exocrine Pancreas?", *Mayo Clinic Proc*, Apr. 1985, vol. 60, pp. 259-265.

Layer et al., "Human pancreatic secretion during phase II antral motility of the interdigestive cycle", *American Physiological Society*, 88 G249-G253 (1988).

Mokdad et al., "Prevalence of Obesity, Diabetes, and Obesity-Related Health Risk Factors, 2001", *JAMA*, vol. 289, No. 1 (Jan. 1, 2003).

Taylor, et al., "Effects of Pancreatic Polypeptide, Caerulein, and Bombesin on Satiety in Obese Mice", *American Journal of Physiology*, 248:G277-G280 (1985).

Balemba et al., "Innervation of the extrahepatic biliary tract", The Anatomical Record Part A: Discoveries in Molecular, Cellular, and Evolutionary Biology; 2004: vol. 280A, Issue 1, pp. 836-847.

Bowen, "Secretion of Bile and the Role of the Bile Acids in Digestion" (2001).

Chang, et al., "Long-Term Results of Duodenectomy with Highly Selective Vagotomy in the Treatment of complicated Duodenal Ulcers", *Amer. J. of Surg.*, vol. 181, pp. 372-376 (2001).

Davidson, et al., "Long-Term Effects of Botulinum Toxin Injections in Spasmodic Dysphonia", *Ann. Otol. Rhinol. Laryngol.*, vol. 105, pp. 34-42 (1996).

Furukawa et al., "Effects of Selective Vagal Stimulation on the Gallbladder and Sphincter of Oddi and Peripheral Vagal Routes Mediating Bile Evacuative Responses Induced by Hypothalamic Stimulation", JJP vol. 42 321-334, (1992).

Hassall et al., "Mechanisms of Gastroesophageal Reflux and Gastroesophageal Reflux Disease", *Journal of Pediatric Gastroenterology and Nutrition*, 35:119-136 (Aug. 2002).

Illustrated Stedman's Medical Dictionary, 24th Edition, Williams & Wilkins, Baltimore, MD, USA, Publisher, title pages and p. 3 (1982).

International Search Report (Partial) mailed Aug. 28, 2008.

International Search Report and Written Opinion mailed Dec. 3, 2008.

International Search Report and Written Opinion mailed Jul. 8, 2009.

International Search Report and Written Opinion mailed May 25, 2009.

Sautter, et al., "Transient Paralysis of the Bladder due to Wound Botulims", *Eur. Urol.*, vol. 39, pp. 610-612 (2001).Sautter, et al., "Transient Paralysis of the Bladder due to Wound Botulism", *Eur. Urol.*, vol. 39, pp. 610-612 (2001).

Sherman, "Obesity and Technology: Can the stomach be fooled", Reuters (Apr. 26, 2006), 3 pages, http://news.yahoo.com/s/nm/20060426/us_nm/bizfeature_obesity_technology_de&printer as printed on May 23, 2006.

The Merck Manual of Diagnosis and Therapy, 18th Edition, Beers, Editor—in-Chief, title page and pp. 128-133 (Merck Research Laboratories 2006).

U.S. Appl. No. 10/674,330 Office Action mailed Apr. 22, 2008.
U.S. Appl. No. 11/040,767 Notice of Allowance dated Jun. 22, 2009.
U.S. Appl. No. 11/656,113 Office Action dated Apr. 6, 2009.
U.S. Appl. No. 11/656,113 Notice of Allowance dated Dec. 7, 2009.
U.S. Appl. No. 11/656,121 Office Action dated Apr. 2, 2009.
U.S. Appl. No. 11/656,122 Notice of Allowance dated Aug. 7, 2009.
U.S. Appl. No. 11/656,123 Office Action dated Dec. 10, 2009.
U.S. Appl. No. 11/656,132 Office Action dated Jul. 20, 2009.
U.S. Appl. No. 11/891,770 Office Action dated Jul. 20, 2009.
U.S. Appl. No. 11/891,770 Notice of Allowance dated Feb. 1, 2010.
U.S. Appl. No. 11/656,121 Office Action dated Dec. 23, 2009.
U.S. Appl. No. 11/656,132 Notice of Allowance dated Jan. 26, 2010.
International Search Report for PCT/US2009/053114 Dated Oct. 26, 2009.

* cited by examiner

HIGH FREQUENCY OBESITY TREATMENT

CROSS-REFERENCE TO RELATED APPLICATIONS

The present application is a continuation-in-part of U.S. patent applications Ser. No. 10/674,324 now abandoned; Ser. No. 10/674,330 now U.S. Pat. No. 7,489,969; and Ser. No. 10/675,818 now abandoned all filed in the name of the present inventors on Sep. 29, 2003 and entitled "Nerve Stimulation And Conduction Block Therapy", "Vagal Down-Regulation Obesity Treatment" and "Nerve Stimulation and Nerve Stimulation and Blocking for Treatment of Gastrointestinal Disorders", respectively, and U.S. patent applications Ser. No. 10/752,940 now U.S. Pat. No. 7,444,183 and Ser. No. 10/752,944 (now U.S. Pat. No. 7,167,750 issued Jan 23, 2007) all filed in the name of the present inventors on Jan 6, 2004 and respectively entitled "Intraluminal Electrode Apparatus and Method" and "Obesity Treatment With Electrically Induced Vagal Down Regulation"; which patent applications are each continuations-in-part of U.S. patent application Ser. No. 10/358,093 filed Feb 3, 2003 (now abandoned) (all of the foregoing collectively referred to herein as the "parent applications"); which parent applications are incorporated herein by reference.

BACKGROUND OF THE INVENTION

1. Field of the Invention

This invention pertains to treatments of disorders associated, at least in part, with neural activity. These may include, without limitation, gastrointestinal, pancreo-biliary, cardio-respiratory and central nervous system disorders (including neurological and psychiatric, psychological and panic disorders). More particularly, this invention pertains to treatment of such disorders through management of neural impulse stimulation and blocking.

2. Description of the Prior Art

As disclosed in the parent applications and their related international patent applications Ser. Nos. PCT/US2004/002847; PCT/US2004/002841 and PCT/US2004/002849 (all incorporated herein by reference), a wide variety of disorders can be treated by blocking neural impulses on the vagus nerves. The blocking can be used as a therapy by itself or used in combination with traditional electrical nerve stimulation. The disorders to be treated include, without limitation, functional gastrointestinal disorders (FGIDs) (such as functional dyspepsia (dysmotility-like) and irritable bowel syndrome (IBS)), gastroparesis, gastroesophageal reflux disease (GERD), inflammation, discomfort and other disorders. Also, the blocking therapy has described application to central nervous system treatments.

Treatments of gastrointestinal diseases through nerve stimulation have been suggested. For example, U.S. Pat. No. 6,238,423 to Bardy dated May 29, 2001 describes a constipation treatment involving electrical stimulation of the muscles or related nerves of the gut. U.S. Pat. No. 6,571,127 to Ben-Haim et al. dated May 27, 2003 describes increasing motility by applying an electrical field to the GI tract. U.S. Pat. No. 5,540,730 to Terry, Jr. et al., dated Jul. 30, 1996 describes a motility treatment involving vagal stimulation to alter GI contractions in response to a sense condition indicative of need for treatment. U.S. Pat. No. 6,610,713 to Tracey dated Aug. 26, 2003 describes inhibiting release of a proinflammatory cytokine by treating a cell with a cholinergic agonist by stimulating efferent vagus nerve activity to inhibit the inflammatory cytokine cascade.

The present invention is an improvement upon a neural blocking therapy as described in the parent applications. Suggestions have been made to block nerves in very specific ways. For example, U.S. Pat. No. 5,188,104 to Wernicke et al. dated Feb. 23, 1993 describes an attempt to inhibit a subset of nerve fibers in the vagus. Specifically, the patent suggests selectively blocking C-fibers of the vagus at a 40 Hz signal. The maximum frequency discussed in this patent is a 150 Hz frequency. To avoid undesired effects of vagal stimulation on organs not targeted by the stimulation, U.S. Pat. No. 6,684,105 to Cohen et al. dated Jan. 27, 2004 describes the use of collision blocks to suppress antidromic effects of stimulation signals. Both of these blocking techniques have significant drawbacks. Subselection of fibers is very difficult in practice. Collision blocking results in a signal being propagated in both afferent and efferent directions. The parent applications teach application of full cross-section neural block to inhibit action potentials across all nerve fibers at a blocked site and thereby blocking both afferent and efferent signals.

The present invention is an improvement upon a neural blocking to avoid antidromic influences during stimulation or to otherwise down-regulate nerve activity. Cryogenic nerve blocking of the vagus is described in Dapoigny et al., "Vagal influence on colonic motor activity in conscious nonhuman primates", *Am. J. Physiol.*, 262: G231-G236 (1992). Electrically induced nerve blocking is described in Van Den Honert, et al., "Generation of Unidirectionally Propagated Action Potentials in a Peripheral Nerve by Brief Stimuli", *Science*, Vol. 206, pp. 1311-1312. An electrical nerve block is described in Solomonow, et al., "Control of Muscle Contractile Force through Indirect High-Frequency Stimulation", *Am. J. of Physical Medicine*, Vol. 62, No. 2, pp. 71-82 (1983) and Petrofsky, et al., "Impact of Recruitment Order on Electrode Design for Neural Prosthetics of Skeletal Muscle", *Am. J. of Physical Medicine*, Vol. 60, No. 5, pp. 243-253 (1981). A neural prosthesis with an electrical nerve block is also described in U.S. Patent Application Publication No. US 2002/0055779 A1 to Andrews published May 9, 2002. A cryogenic vagal block and resulting effect on gastric emptying are described in Paterson C A, et al., "Determinants of Occurrence and Volume of Transpyloric Flow During Gastric Emptying of Liquids in Dogs: Importance of Vagal Input", *Dig Dis Sci*, (2000);45:1509-1516.

Constant nerve blocking (through constant blocking signal application) can be undesirable. Such a treatment can have high power requirements. Furthermore, a complete down-regulation of a nerve can be undesirable since the nerve's desirable functions are also interrupted. It would be desirable to more fully control the degree of down-regulation of a nerve to achieve a desired therapy while minimizing undesired effects of complete or constant down-regulation.

SUMMARY OF THE INVENTION

A method is disclosed for treating at least one of a plurality of disorders of a patient where the disorders are characterized at least in part by vagal activity innervating at least one of a plurality of alimentary tract organs of the patient at an innervation site. The method includes positioning a neurostimulator carrier around a body organ of the patient where the organ is innervated by at least a vagal trunk or branch and with an electrode disposed on the carrier and positioned at the vagal trunk or branch. An electrical signal is applied to the electrode to modulate vagal activity by an amount selected to treat the disorder. The electrical signal is applied at a frequency selected for the signal to create a neural conduction block to the trunk or branch at a blocking site with the neural conduction block selected to at least partially block nerve impulses on the trunk at the blocking site. The application of the electrical signal is discontinued. The application of the signal and the discontinuing of the signal are repeated with durations of the discontinuing and the application selected to treat the disorder.

DESCRIPTION OF THE PREFERRED EMBODIMENT

With reference now to the various drawing figures in which identical elements are numbered identically throughout, a description of the preferred embodiment of the present invention will now be described.

Description of Prior Applications

The parent applications and the afore-mentioned related international applications (all incorporated herein by reference) teach various aspects of stimulating and blocking electrodes for either up-regulating or down-regulating the vagus nerve and combinations of these electrodes for a wide variety of therapies. To facilitate an understanding of the present invention, selected portions of those applications are described in this section.

1. Description of Vagal Innervation of the Alimentary Tract

Figure 1:
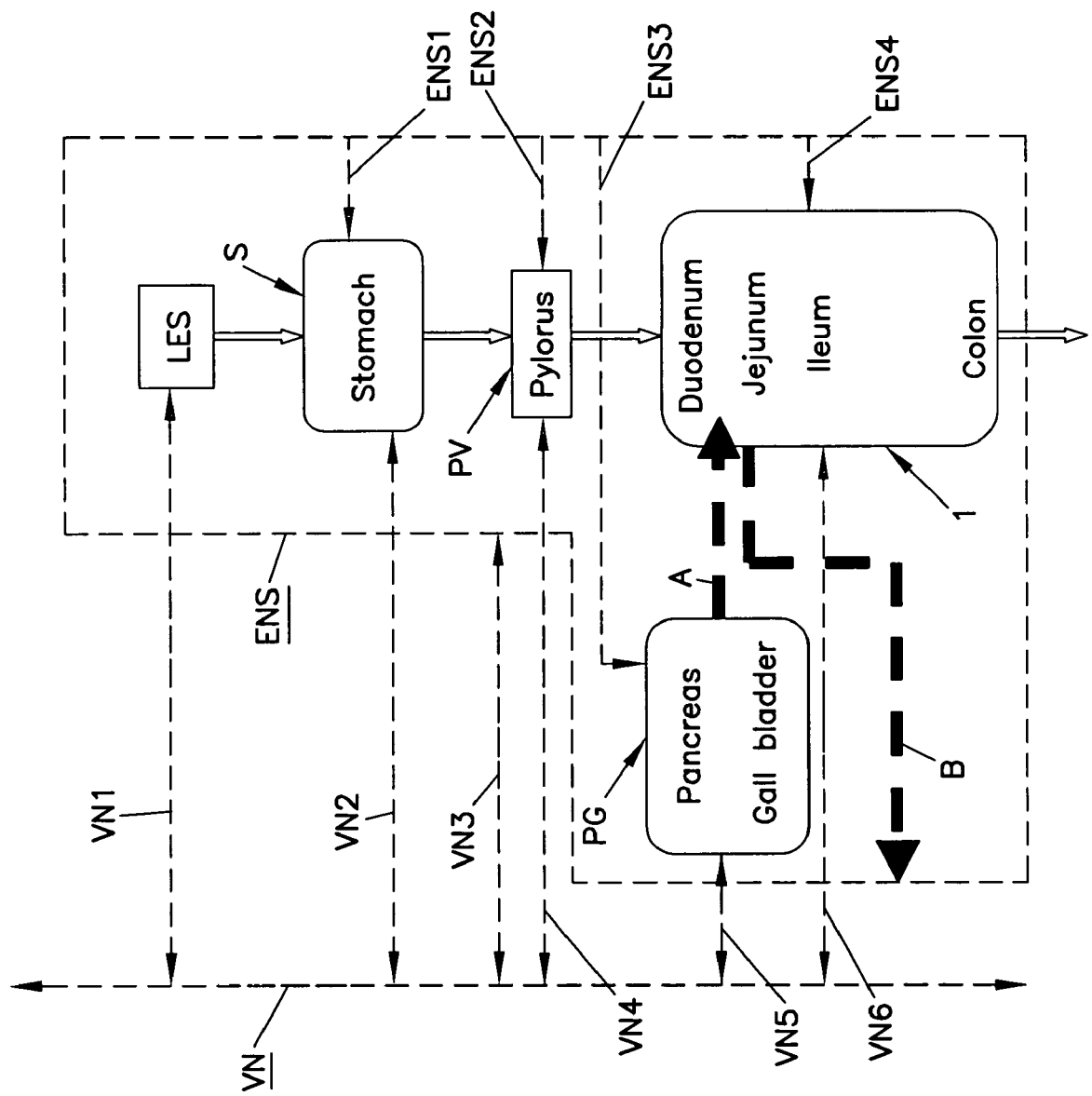
FIG. 1 is a schematic illustration of an alimentary tract (GI tract plus non-GI organs such as the pancreas and liver) and its relation to vagal and enteric innervation.

FIG. 1 is a schematic illustration of an alimentary tract (GI tract plus non-GI organs such as the pancreas and ball bladder, collectively labeled PG) and its relation to vagal and enteric innervation. The lower esophageal sphincter (LES) acts as a gate to pass food into the stomach S and, assuming adequate function of all components, prevent reflux. The pylorus PV controls passage of chyme from the stomach S into the intestines I (collectively shown in the figures and including the large intestine or colon and the small intestine including the duodenum, jejunum and ileum).

The biochemistry of the contents of the intestines I is influenced by the pancreas P and gall bladder PG which discharge into the duodenum. This discharge is illustrated by dotted arrow A.

Figure 3:
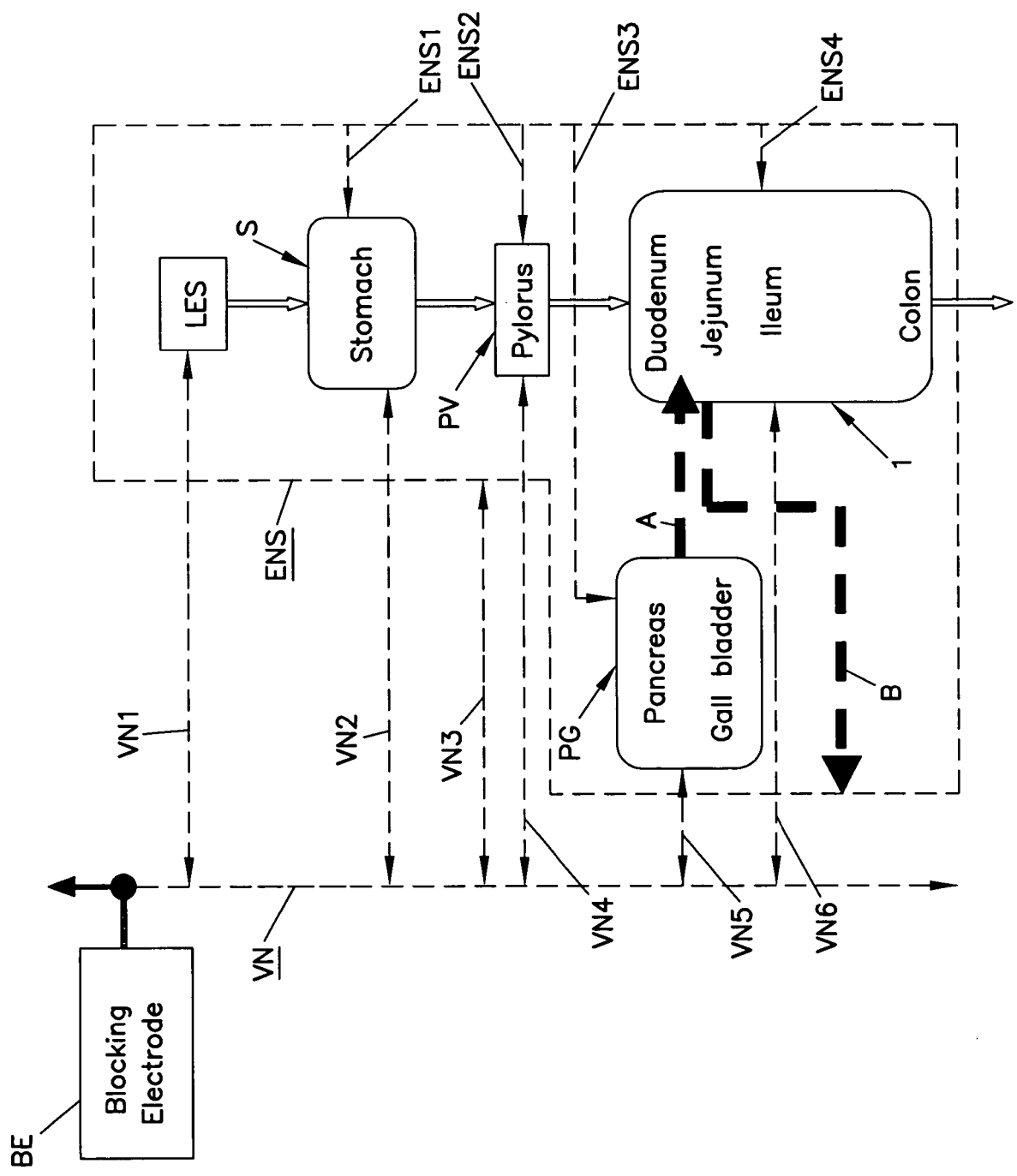
FIG. 3 is the view of FIG. 1 showing the application of a nerve conduction block electrode to the alimentary tract.
Figure 13:
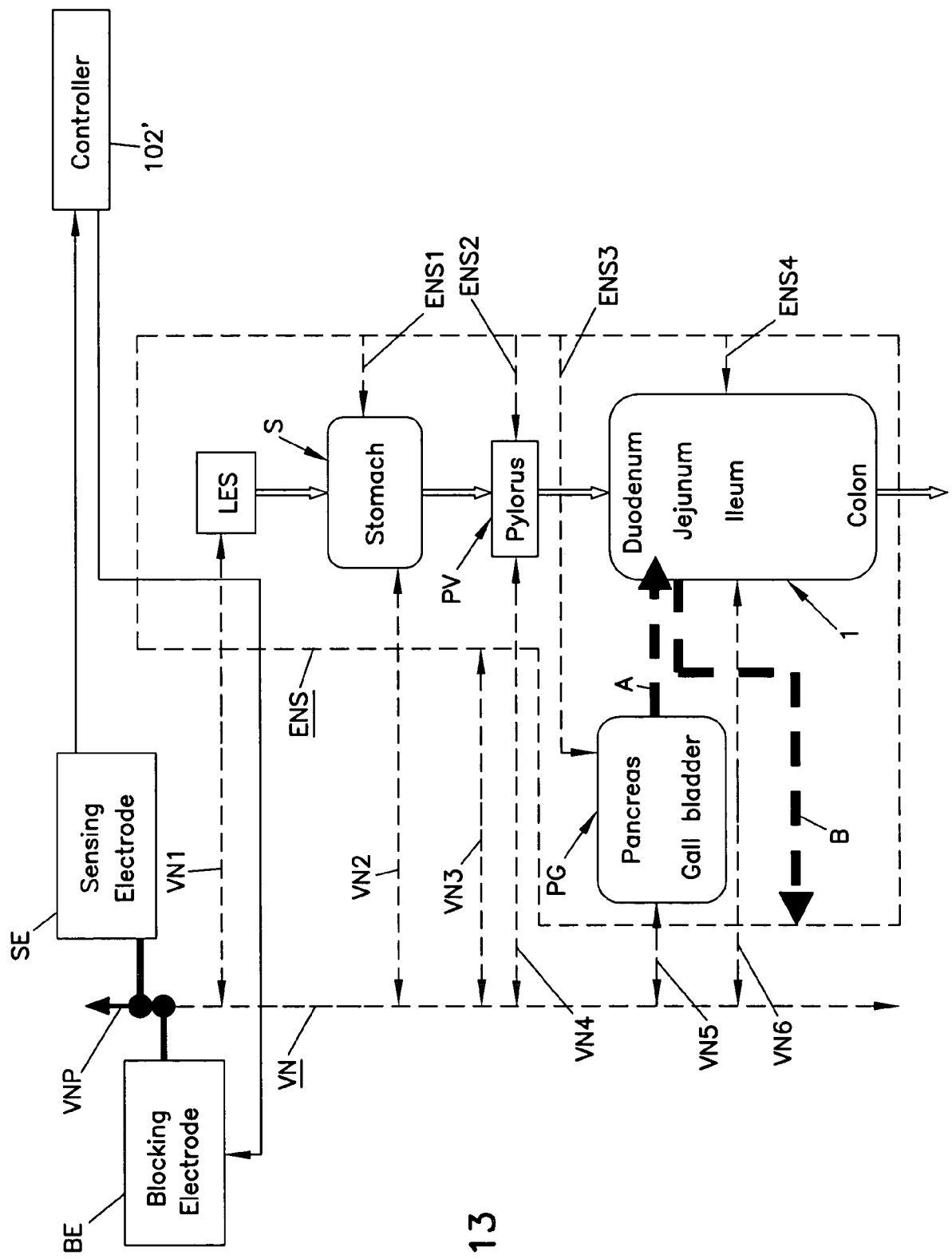
FIG. 13 is a view similar to that of FIG. 3 showing the addition of a sensing electrode and controller according to the present invention.

The vagus nerve VN transmits signals to the stomach S, pylorus PV, pancreas and gall bladder PG directly. Originating in the brain, there is a common vagus nerve VN in the region of the diaphragm (not shown). In the region of the diaphragm, the vagus VN separates into anterior and posterior components with both acting to innervate the GI tract. In FIGS. 1, 3 and 13, the anterior and posterior vagus nerves are not shown separately. Instead, the vagus nerve VN is shown schematically to include both anterior and posterior nerves.

The vagus nerve VN contains both afferent and efferent components sending signals to and away from, respectively, its innervated organs.

In addition to influence from the vagus nerve VN, the GI and alimentary tracts are greatly influenced by the enteric nervous system ENS. The enteric nervous system ENS is an interconnected network of nerves, receptors and actuators throughout the GI tract and pancreas and gall bladder PG. There are many millions of nerve endings of the enteric nervous system ENS in the tissues of the GI organs. For ease of illustration, the enteric nervous system ENS is illustrated as a line enveloping the organs innervated by the enteric nervous system ENS The vagus nerve VN innervates, at least in part, the enteric nervous system ENS (schematically illustrated by vagal trunk VN3 which represents many vagus-ENS innervation throughout the cut). Also, receptors in the intestines I connect to the enteric nervous system ENS. Arrow B in the figures illustrates the influence of duodenal contents on the enteric nervous system ENS as a feedback to the secretion function of the pancreas, liver and gall bladder. Specifically, receptors in the intestine I respond the biochemistry of the intestine contents (which are chemically modulated by the pancreao-biliary output of Arrow A). This biochemistry includes pH and osmolality.

In the figures, vagal trunks VN1, VN2, VN4 and VN6 illustrate schematically the direct vagal innervation of the GI organs of the LES, stomach S, pylorus PV and intestines I. Trunk VN3 illustrates direct communication between the vagus VN and the ENS. Trunk VN5 illustrates direct vagal innervation of the pancreas and gall bladder. Enteric nerves ENS1-ENS4 represent the multitude of enteric nerves in the stomach S, pylorus PV, pancreas and gall bladder PG and intestines I.

While communicating with the vagus nerve VN, the enteric nervous system ENS can act independently of the vagus and the central nervous system. For example, in patients with a severed vagus nerve (vagotomy—an historical procedure for treating ulcers), the enteric nervous system can operate the gut. Most enteric nerve cells are not directly innervated by the vagus. Gershon, "The Second Brain", Harper Collins Publishers, Inc, New York, N.Y. p. 19 (1998)

2. Implantable Pacing Circuit

Figure 2:
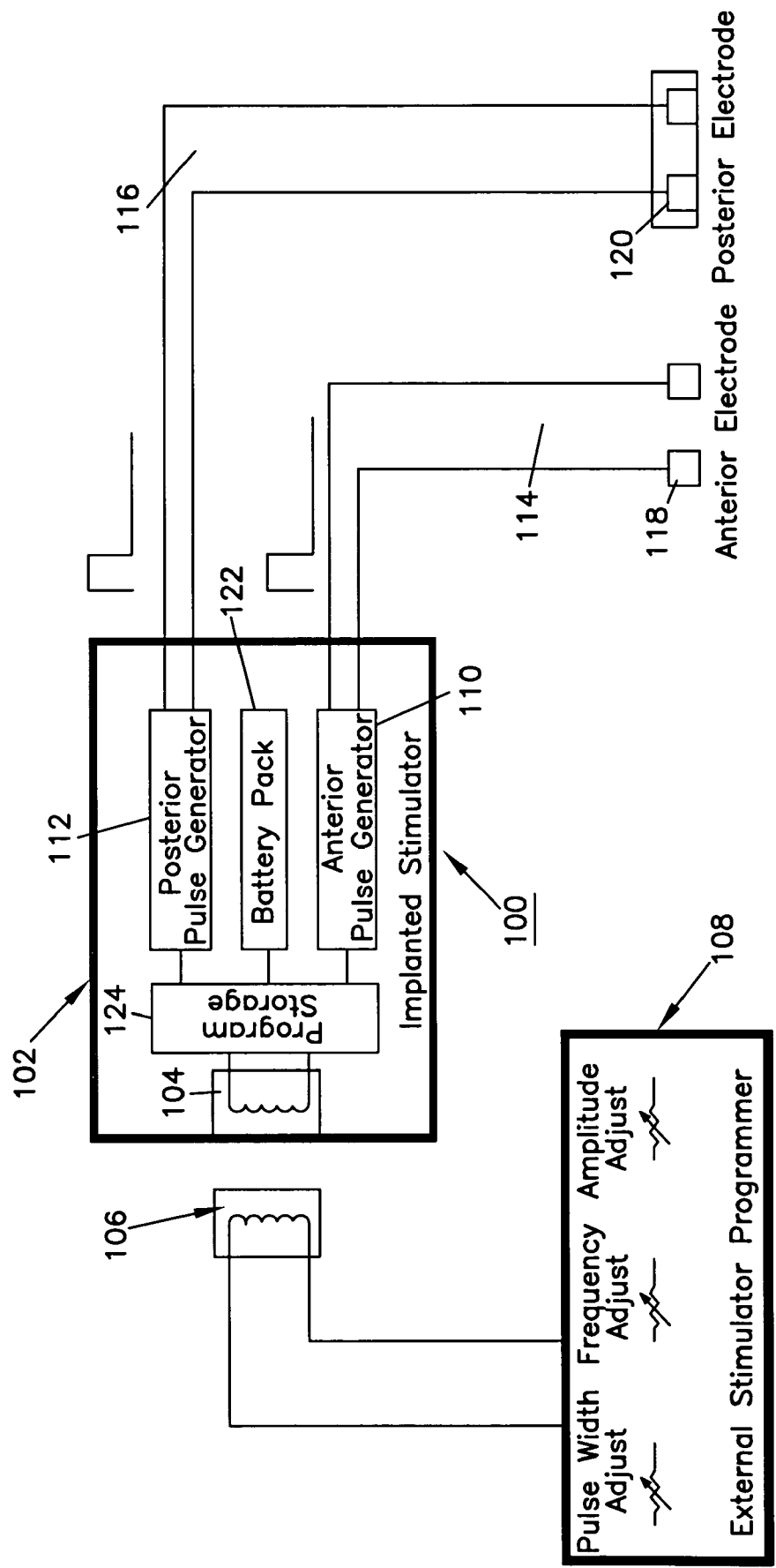
FIG. 2 is a schematic representation of pacing system.

A representative pacing circuit 100 is schematically shown in FIG. 2. Similar to cardiac pacing devices, an implantable controller 102 contains an induction coil 104 for inductive electrical coupling to a coil 106 of an external controller 108. The implantable controller 102 includes anterior and posterior pulse generators 110, 112 electrically connected through conductors 114, 116 to anterior and posterior pacing electrodes 118, 120 for attachment to anterior and posterior trunks, respectively, of the vagus nerve VN. The implantable controller 102 also includes a battery 122 and a CPU 124 which includes program storage and memory. The timing and parameters of the pulse at the electrodes 118, 120 can be adjusted by inductively coupling the external controller 108 to the implantable controller 102 and inputting pacing parameters (e.g., pulse width, frequency and amplitude).

While a fully implantable controller 102 is one possible embodiment, it is not necessary. For example, the electrodes 118, 120 can be implanted connected to a receiving antenna placed near the body surface. The control circuits (i.e., the elements 124, 110, 112 and 108) can be housed in an external pack worn by the patient with a transmitting antenna held in place on the skin over the area of the implanted receiving antenna. Such a design is forward-compatible in that the implanted electrodes can be later substituted with the implantable controller 102 at a later surgery if desired.

Although not shown in FIG. 2, the controller 102 can also include circuits generating nerve conduction block signals (as will be described) which connect to electrodes which may be positioned on a nerve proximally, distally (or both) of the electrodes 118, 120.

3. Neural Blocking Therapy

FIG. 3 illustrates a therapy application using a nerve conduction blocking electrode for providing a conduction block. A nerve block is, functionally speaking, a reversible vagotomy. Namely, application of the block at least partially prevents nerve transmission across the site of the block. Removal of the block restores normal nerve activity at the site. A block is any localized imposition of conditions that at least partially diminish transmission of impulses.

The block may be intermittent or continuous. The preferred nerve conduction block is an electronic block created by a signal at the vagus by an electrode PBE controlled by the implantable controller (such as controller 102 or an external controller). The nerve conduction block can be any reversible block. For example, ultrasound, cryogenics (either chemically or electronically induced) or drug blocks can be used. An electronic cryogenic block may be a Peltier solid-state device which cools in response to a current and may be electrically controlled to regulate cooling. Drug blocks may include a pump-controlled subcutaneous drug delivery.

With such an electrode conduction block, the block parameters (signal type and timing) can be altered by a controller and can be coordinated with the pacing signals to block only during pacing. A representative blocking signal is a 500 Hz signal with other parameters (e.g., timing and current) matched to be the same as the pacing signal. While an alternating current blocking signal is described, a direct current (e.g., −70 mV DC) could be used.

The foregoing specific examples of blocking signals are representative only. Other examples and ranges of blocking signals are described in the afore-mentioned literature. For example, the nerve conduction block is preferably within the parameters disclosed in Solomonow, et al., "Control of Muscle Contractile Force through Indirect High-Frequency Stimulation", *Am. J. of Physical Medicine*, Vol. 62, No. 2, pp. 71-82 (1983). Particularly, the nerve conduction block is applied with electrical signal selected to block the entire cross-section of the nerve (e.g., both afferent, efferent, myelinated and nonmyelinated fibers) at the site of applying the blocking signal (as opposed to selected sub-groups of nerve fibers or just efferent and not afferent or visa versa) and, more preferably, has a frequency selected to exceed the 200 Hz threshold frequency described in Solomonow et al. Further, preferred parameters are a frequency of 500 Hz (with other parameters, as non-limiting examples, being amplitude of 4 mA, pulse width of 0.5 msec, and duty cycle of 5 minutes on and 10 minutes off). As will be more fully described, the present invention gives a physician great latitude in selected pacing and blocking parameters for individual patients.

In certain patients, the vagus nerve activity may contribute to undesired effects such pancreatitis progression or obesity contributing factors. Use of a blocking electrode alone in the vagus permits down-regulating the vagus nerve VN, the enteric nervous system ENS and pancreo-biliary output. The block down-regulates both afferent and efferent signal transmission.

In FIG. 3, the baseline vagal activity is illustrated by the solid line of the proximal vagus nerve segment VNP. The remainder of the vagus and enteric nervous system are shown in reduced thickness to illustrate down-regulation of tone. The pancreo-biliary output (and resulting feedback) is also reduced. In FIG. 3, the blocking electrode BE is shown high on the vagus relative to the GI tract innervation (e.g., just below the diaphragm), the sole blocking electrode could be placed lower (e.g., just proximal to pancreo/biliary innervation VN5). Blocking of the entire vagus as described above can be used to down-regulate the vagus for various benefits including: pancreatitis and obesity treatments. Further, blocking the vagus interrupts the vagally-mediated neurogenic inflammatory arc.

The use of blocking as an independent therapy permits treatment for pancreatitis and obesity by down regulating vagal activity and pancreatic output including pancreatic exocrine secretion. Also, the blocking may be used as a separate treatment for reducing discomfort and pain associated with gastrointestinal disorders or other vagally mediated pain (i.e., somatic pain sensations transmitted along any nerve fibers with pain sensation modulated by vagal afferent fibers). A nerve stimulation to treat pain is described in U.S. patent application publication No. US2003/0144709 to Zabara et al., published Jul. 31, 2003.

4. Application to Obesity

Obesity is treatable with vagal block. Recent literature describes potential obesity treatments relative to gut hormone fragment peptide $YY_{3-36}$. See, e.g., Batterham, et al., "Inhibition of Food Intake in Obese Subjects by Peptide YY3-36", *New England J. Med.*, pp. 941-948 (Sep. 4, 2003) and Komer et al., "To Eat or Not to Eat—How the Gut Talks to the Brain", *New England J. Med., pp.* 926-928 (Sep. 4, 2003). The peptide $YY_{3-36}$ (PPY) has the effect of inhibiting gut motility through the phenomena of the ileal brake. Vagal afferents create a sensation of satiety.

The present invention can electrically simulate the effects of PPY by using the vagal block to down-regulate afferent vagal activity to create a desired sensation of satiety. Since the down-regulation does not require continuous blocking signals, the beneficial efferent signals are permitted.

Also, vagal block restricts fundal accommodation, reduces pancreatic exocrine secretion (thereby reducing caloric absorption) and beneficially effects both satiety and satiation.

5. Apparatus for Applying Vagal Block a. Background

Figure 4:
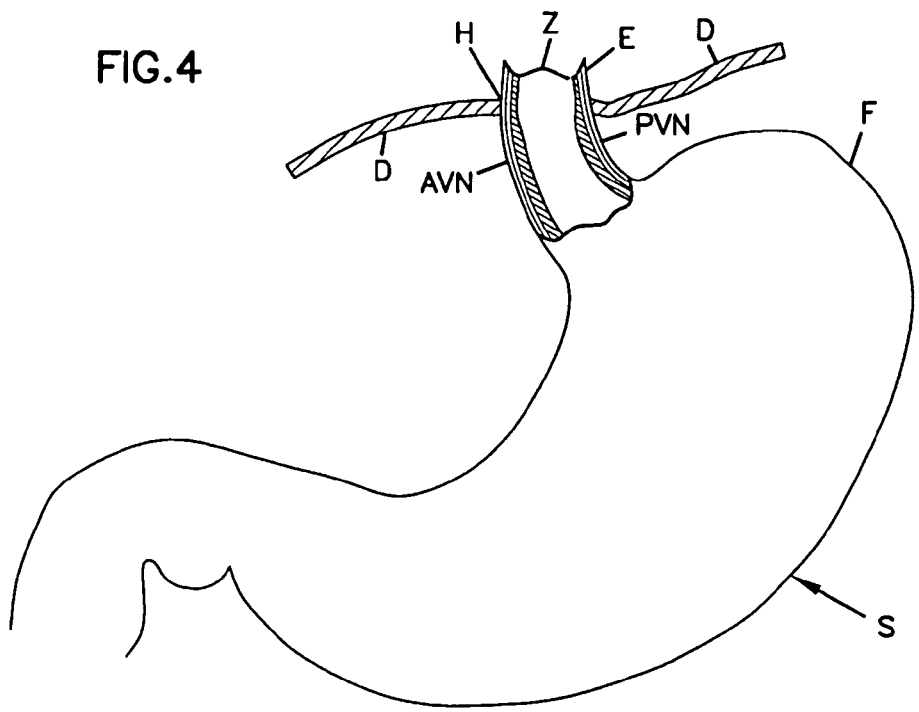
FIG. 4 is a schematic representation of a patients' stomach shown partially in section and illustrating a representative placement of anterior and posterior vagus nerves with respect to the anatomy of the stomach and diaphragm.
Figure 7:
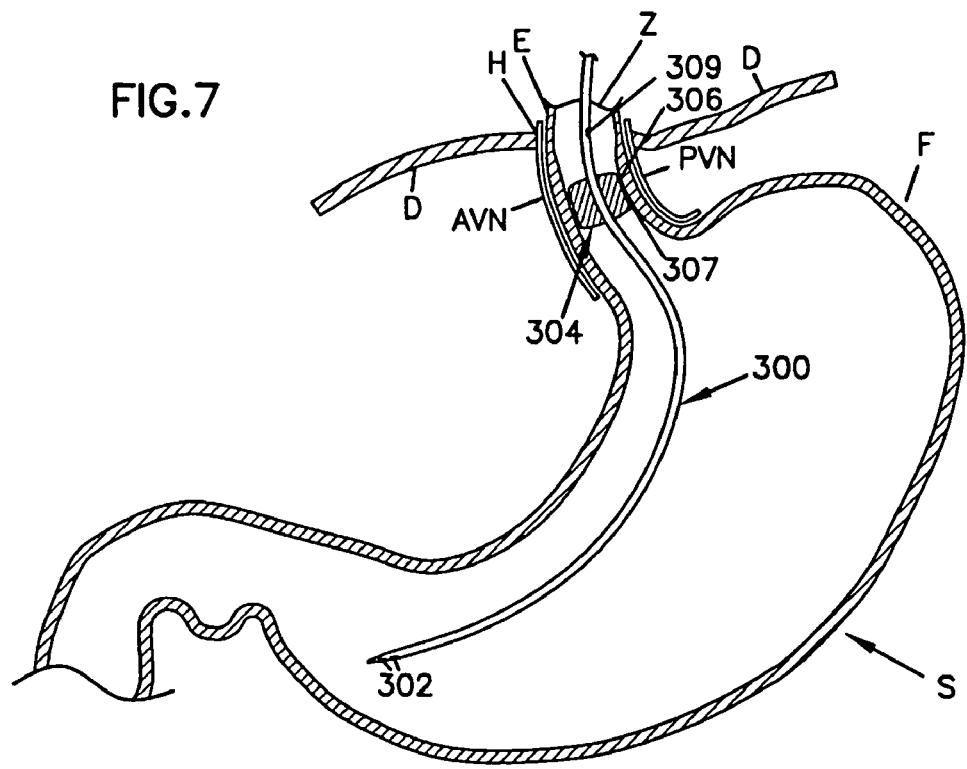
FIG. 7 is a side sectional view of a patients' stomach illustrating a transesophageal electrode.

With reference to FIG. 4, a stomach S is shown schematically for the purpose of facilitating an understanding of applying a blocking signal as illustrated in FIGS. 5 -12. In FIG. 4, the stomach S is shown with a collapsed fundus F which is deflated due to fasting. In practice, the fundus F can be reduced in size and volume (as shown in FIG. 4) or expanded (as shown in FIG. 7).

The esophagus E passes through the diaphragm D at an opening or hiatus H. In the region where the esophagus E passes through the diaphragm D, trunks of the vagal nerve (illustrated as the anterior vagus nerve AVN and posterior vagus nerve PVN) are disposed on opposite sides of the esophagus E. It will be appreciated that the precise location of the anterior and posterior vagus nerves AVN, PVN relative to one another and to the esophagus E are subject to a wide degree of variation within a patient population. However, for most patients, the anterior and posterior vagus nerves AVN, PVN are in close proximity to the esophagus E at the hiatus H where the esophagus E passes through the diaphragm D.

The anterior and posterior vagus nerves AVN, PVN divide into a plurality of trunks that innervate the stomach directly and via the enteric nervous system and may include portions of the nerves which may proceed to other organs such as the pancreas, gallbladder and intestines. Commonly, the anterior and posterior vagus nerves AVN, PVN are still in close proximity to the esophagus E and stomach (and not yet extensively branched out) at the region of the junction of the esophagus E and stomach S.

In the region of the hiatus H, there is a transition from esophageal tissue to gastric tissue. This region is referred to as the Z-line (labeled "Z" in the Figures). Above the Z-line, the tissue of the esophagus is thin and fragile. Below the Z-line, the tissue of the esophagus E and stomach S are substantially thickened and more vascular. Within a patient population, the Z-line is in the general region of the lower esophageal sphincter. This location may be slightly above, slightly below or at the location of the hiatus H.

b. Implanted Band Electrode i. Description of Device

Figure 5:
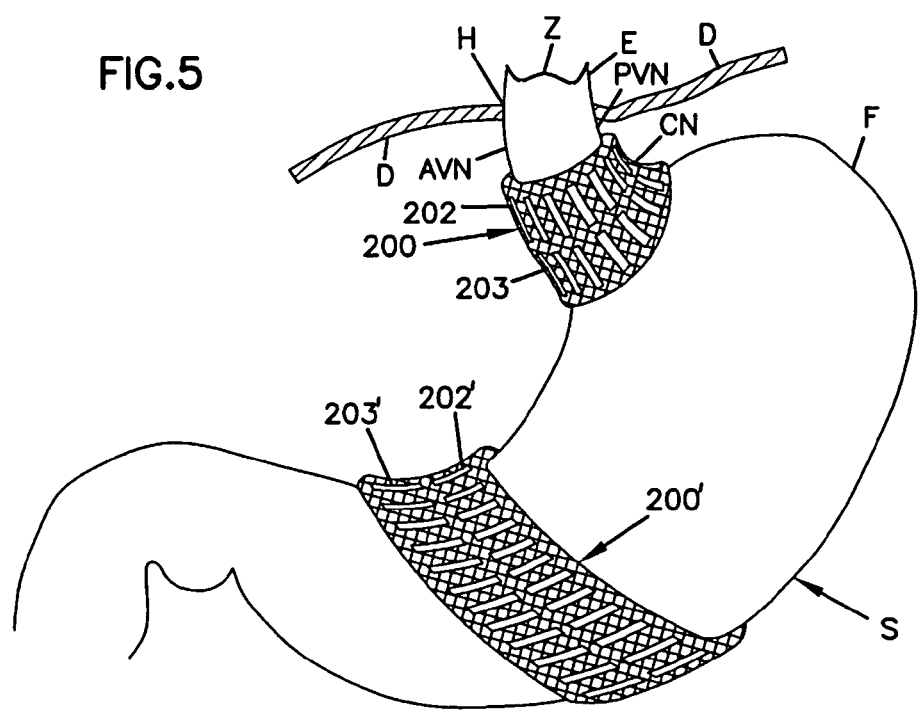
FIG. 5 is the view of FIG. 4 showing placement of electrode bands.
Figure 6:
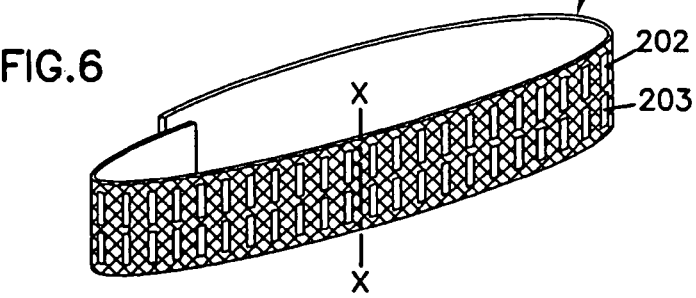
FIG. 6 is a perspective view of a band used in FIG. 5.

With reference to FIG. 5, a band 200 is shown placed around the esophagus E or proximal portion of the stomach below the diaphragm D and overlying the anterior and posterior vagus nerves AVN, PVN at the cardiac notch CN. Alternatively, it can be placed completely around the upper portion of the stomach near its junction of the esophagus. Placement of a band 200 around the esophagus E directly beneath the diaphragm D ensures that the band may be placed around the anterior and posterior vagus nerves AVN, PVN without the need for extensive dissection of the nerves AVN, PVN. In a preferred embodiment, the nerves AVN, PVN are indirectly stimulated by passing electrical signals through the tissue surrounding the nerves.

The band 200 may be formed of polyester or the like or any other suitable material which may be sutured in place or otherwise fastened in place surrounding the esophagus E or gastric cardia. Preferably, the band 200 is placed at the junction of the esophagus E and stomach S such that the band may overly both the esophagus E and stomach S at the cardiac notch CN.

Figure 11:
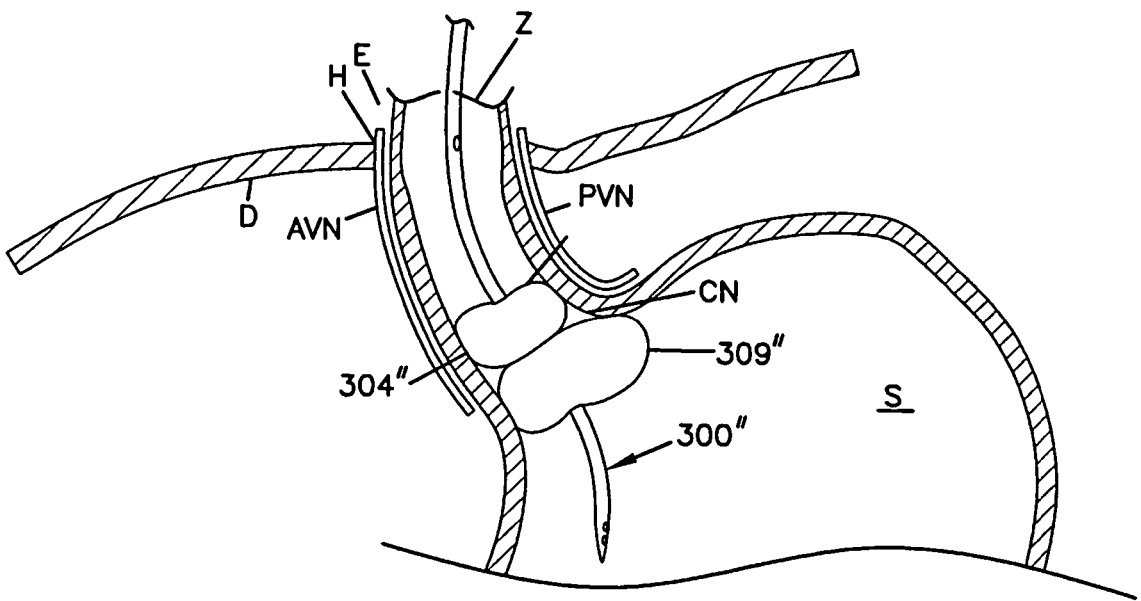
FIG. 11 is a side sectional view of a patients' stomach in illustrating a still further alternative apparatus of FIG. 8.

The band 200 may have a plurality of electrodes which, in the embodiment of FIG. 5 include an upper electrode array 202 and a lower electrode array 203. In the embodiment of FIG. 11 (in which a band 200 is shown lying flat), the electrode arrays 202, 203 are shown with electrodes placed at an angle relative to the cylindrical axis X-X of the band 200.

Placement of the band 200 as described ensures that at least a subset of the electrodes 202, 203 will be in overlying relation to the anterior and posterior vagus nerves AVN, PVN. As a result, energizing the electrodes 202, 203 will result in stimulation of the anterior and posterior vagus nerves AVN, PVN and/or their branches.

In therapeutic applications, the upper array 202 of electrodes may be connected to a blocking electrical signal source (with a blocking frequency and other parameters as previously described) and the lower array 203 of electrodes may be connected to a stimulation electrical signal source as previously described. Of course, only a single array of electrodes could be used with all electrodes connected to either a blocking or a stimulating signal.

In a preferred embodiment for treating obesity, only upper band 200 is used with both of electrodes 202, 203 being bi-polar pairs (i.e., alternating anode and cathode electrodes) for applying a blocking signal as will be described.

The electrical connection of the electrodes 202, 203 to a controller is not shown but may be as previously described by having a leads connecting the electrodes directly to an implantable controller. Alternatively, and as previously described, electrodes may be connected to an implanted antenna for receiving a signal to energize the electrodes.

The use of an array of electrodes permits the collar 200 to be placed without the need for great accuracy at the time of placement. In the event it is desirable that electrodes not directly overlying a vagus nerve be deactivated, the electrodes could, through operation of a controller, be individually energized to detect a physiological response. The absence of a physiological response (other than possible muscular action of the stomach and esophagus) would indicate the absence of an overlying relation to a vagus nerve. The presence of a physiological response would indicate overlying relation of the tested electrode to a vagus nerve.

By identifying which electrodes create a physiologic response, the remaining electrodes (i.e., those not having a physiological response) could be permanently deactivated. An example of a physiological response would be a cardiovascular response which may be attributed to a signal of about 2-80 hertz and up to 50 milliamps and as more fully described in U.S. Pat. No. 6,532,388 to Hill et al dated Mar. 11, 2003. As a result, a selected one of the AVN or PVN could be energized.

It will be appreciated the foregoing description of identifying electrodes to be deactivated is a non-limiting embodiment. For example, all electrodes could be energized. The therapies as previously described could be employed by using blocking electrodes or stimulation electrodes or both in order to block or energize (or both) the vagus nerve.

FIG. 5 also illustrates an alternative embodiment in the form of a band 200' surrounding the body of the stomach S and having arrays 202', 203'. Since the band 200' is more distal to the esophagus E, different and more distal trunks of the vagus nerves would be energized. Also, such a placement would permit the option of covering the anterior vagus nerve while not covering the posterior vagus nerve (or visa versa).

In addition to the benefits of nerve pacing, the band 200 can also be used to restrict and potentially lengthen the esophagus thereby reducing possibilities for reflux as more fully described in commonly assigned and co-pending U.S. patent application Ser. No. 10/600,088 filed Jun. 20, 2003 and entitled "Gastro-Esophageal Reflux Disease" (GERD) Treatment Method and Apparatus".

An alternative placement of the band is to place the band at the cardia-esophagus junction or at the top of the cardia over-lying a fat pad which surrounds a patient's cardia. Such a placement is used in placing restrictive bands such as the Lap-Band or the Swedish Band of Obtech Medical, AG. So placed, the band 200 covers both anterior and posterior vagal trunks. In most patients, this placement will result in the band 200 not covering the hepatic branch of the vagus. However, the hepatic branch is believed to have little impact on gastric or pancreatic function.

ii. Application to Obesity and Satiety

The embodiment of FIG. 5 is particularly suitable for the treatment of obesity. Obesity is of epidemic proportions and is associated with large decreases in life expectancy and early mortality. Peeters, et al., "Obesity in Adulthood and Its Consequences for Life Expectancy: A Life Table Analysis", *Annals of Internal Medicine*, Vol. 138, No. 1, pp. 24-32 (2003).

In the embodiment of FIG. 5, the upper band 200 is placed around the stomach near the cardiac notch CN. Electrode array 202 may be de-activated (or not present on the band 200). Lower array 203 can be energized with a blocking signal.

The prior art suggests stimulating the vagas with a stimulating signal for treating obesity or eating disorders. See, e.g., U.S. Pat. No. 5,188,104 to Wernicke et al., dated Feb. 23, 1993; U.S. Pat. No. 5,263,480 to Wernicke et al., dated Nov. 23, 1993; U.S. Pat. No. 6,587,719 to Barrett et al., dated Jul. 1, 2003 and U.S. Pat. No. 6,609,025 to Barrett et al., dated Aug. 19, 2003. These patents all describe stimulating, non-blocking signals (e.g., stimulating to a level slightly below a so-called "retching threshold" as described in the '025 patent). As such, all fail to note the problem associated with obesity and eating discords that is not addressed by stimulating the vagus but, rather, by blocking stimulation on the vagus.

The blocking at cardiac notch CN reduces fundal accommodation and creates satiety sensations. Such a physiologic response is suggested by vagotomy data in which truncal vagotomy patients have experienced weight loss and increased satiety. See, e.g., Kral, "Vagotomy as a Treatment for Morbid Obesity", *Surg. Clinics of N. Amer.*, Vol. 59, No. 6, pp. 1131-1138 (1979), Gortz, et al., "Truncal Vagotomy Reduces Food and Liquid Intake in Man", *Physiology & Behavior*, Vol. 48, pp. 779-781 (1990), Smith, et al., "Truncal Vagotomy in Hypothalamic Obesity", *The Lancet*, pp. 1330-1331 (1983) and Kral, "Vagotomy for Treatment of Severe Obesity", *The Lancet*, pp. 307-308 (1978).

The optional lower band 200' is placed lower on the stomach (e.g., close to the pylorus). The lower electrode array 203' of the lower band 200' is energized with a stimulation signal to modulate intestinal motility in the event motility is otherwise impaired by the upper band blocking.

The upper array 202' of the lower band 200' is energized with a blocking signal so that the stimulation signal at electrodes 203' does not interfere with the blocking effect of electrodes 203 of upper band 200. In this obesity treatment, the electrodes of the bands 200, 200' can be placed on constricting bands (such as the well-known Lap-Band® system of Inamed Inc., Santa Barbara, Calif., USA, and used in obesity treatment or the previously mentioned and similarly used Swedish band). More preferably, the bands 200, 200' are not constricting thereby minimizing erosion risks otherwise associated with highly constricting bands. However, the neural blocking technology of the present invention can be incorporated into such constricting bands or used in conjunction other obesity surgeries or therapies. Specifically, the scientific literature indicates a vagotomy in combination with other obesity procedure (e.g., antrectomy, gastroplasty and biliopancreatic bypass) improves weight loss procedures. Tzu-Ming, et al., "Long-Term Results of Duodenectomy with Highly Selective Vagotomy in the Treatment of complicated Duodenal Ulcers", *Amer. J. of Surg.*, Vol. 181, pp. 372-376 (2001), Kral, et al., "Gastroplasty for Obesity: Long-Term Weight Loss Improved by Vagotomy", *World J. Surg.*, Vol. 17, pp. 75-79 (1993), and Biron, et al., "Clinical Experience with Biliopancreatic Bypass and Gastrectomy or Selective Vagotomy for Morbid Obesity", *Canadian J. of Surg.*, Vol. 29, No. 6, pp. 408-410 (1986).

Vagal neural blocking simulates a vagotomy but, unlike a vagotomy, is reversible and controllable. Therefore, while obesity is particularly described as a preferred treatment, the vagal neural block of the present invention can be used as a less drastic procedure for treatments previously performed with a vagotomy. Without limitation, these include obesity, ulcers or chronic pain or discomfort (alone or in combination with conjunctive procedures).

Further, bulimia has been identified as a disease amenable to treatment by decreasing afferent vagal activity via pharmacological vagal inhibitors delivered systemically. Faris, et al., "Effect of Decreasing Afferent Vagal Activity with Ondansetron on Symptoms of Bulimia Nervosa: a Randomized, Double-Blind Trial", *The Lancet*, pp. 792-797 (2000). Therefore, bulimia and other diseases treatable with vagal blocker drugs can be treated with the targeted and site-specific vagal neural block of the present invention.

c. Acute Treatment Device i. Device Description

FIG. 7 illustrates a still further embodiment of the present invention where a nasogastric tube 300 is passed into the stomach. It will be appreciated that nasogastric tubes are well known and form no part of this invention per se. Some nasogastric tubes have specialized functions. An example is a tamponade tube having gastric and esophageal balloons. An example of such is the Bard® Minnesota Four Lumen Esophagogastric Tamponade Tube for the Control of Bleeding from Esophageal Varices as described in product literature (information for use) contained with the product of that name dated 1998 by C. R. Bard, Inc., Covington, Ga., USA. Further, while a nasogastric tube is a preferred embodiment other devices (e.g., an orogastric tube or any elongated device to position electrodes near the esophagus/stomach junction) could be used. Also, while placement at the esophagus/stomach junction is preferred, the device can be placed in a different lumen (e.g., the trachea) for transmucosal stimulation.

The nasogastric tube 300 is multi-lumen tube which includes distal openings 302 to which suction can be applied to remove gastric contents through the tube 300. A compliant balloon 304 surrounds the gastric tube. Proximal to the balloon 304 is an opening 309 in communication with a lumen (not shown) to which a suction can be applied to remove saliva through the opening 309.

Figure 14:
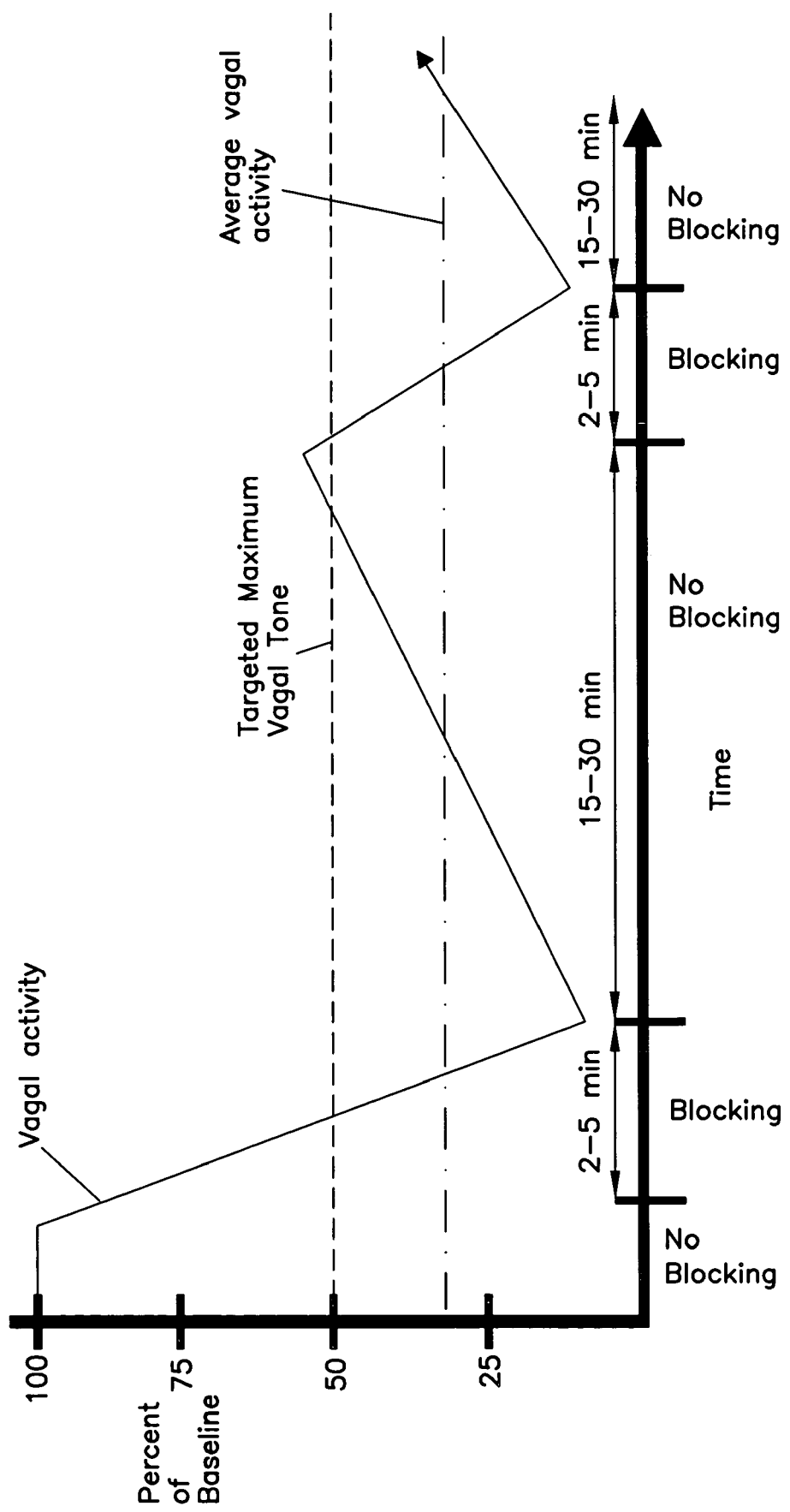
FIG. 14 is a graphical presentation of a controlled vagal activity achieved with the present invention.

The balloon 304 has a plurality of electrodes which may include an upper array 306 of electrodes and a lower array 307 of stimulation electrodes. The electrodes of the upper array 306 may be connected to a blocking signal source via conductors 306a (FIG. 13). The electrodes of the lower array 307 may be connected to a stimulation signal source via conductors 307a. The conductors 306a, 307a may be passed through a lumen in the tube 300 to an external controller (not shown). As a result, multiple electrodes can be energized for transmucosal stimulation of the anterior and posterior vagus nerves AVN, PVN. FIG. 14 shows an alternative design where the arrays 306, 307 are replaced with expandable, circumferential electrodes 306', 307' connected to a controller (not shown) by conductors 306a', 307a'.

As in the embodiment of FIG. 7, the individual electrodes of the arrays 306, 307 may optionally be selectively energized to detect a cardiovascular signal indicating an electrical coupling of the electrodes to the vagus nerves AVN, PVN. Electrodes that do not create such a coupling may optionally be deactivated such that only the electrodes having an effective coupling with the vagus nerves AVN, PVN will be activated. Also, and as in the embodiment of FIG. 7, there may be a single array of electrodes or all electrodes may be energized with either a blocking or stimulation signal.

It will be noted in this embodiment that the electrodes are disposed abutting the mucosal surface of the esophageal and stomach lining and are not in direct contact with the vagus nerves AVN, PVN. Instead, the electrodes are spaced from the vagus nerves AVN, PVN by the thickness of the stomach and lower esophageal wall thickness.

Transmucosal electrical stimulation of nerves is well known. Such stimulation is disclosed in U.S. Pat. No. 6,532, 388 to Hill et al dated Mar. 11, 2003 (describing transmucosal stimulation of nerves across a trachea using a balloon with electrodes in the trachea to modulate cardiac activity). Also, the phenomena of transmucosal electrical stimulation of nerves is described in Accarino, et al, "Symptomatic Responses To Stimulation Of Sensory Pathways In The Jejunum", *Am. J. Physiol.*, Vol. 263, pp. G673-G677 (1992) (describing afferent pathways inducing perception selectively activated by transmucosal electrical nerve stimulation without disruption of intrinsic myoelectrical rhythm); Coffin, et al, "Somatic Stimulation Reduces Perception Of Gut Distention In Humans", *Gastroenterology*, Vol. 107, pp. 1636-1642 (1994); Accarino, et al, "Selective Dysfunction Of Mechano Sensitive Intestinal Afferents In Irritable Bowel Syndrome", *Gastroenterology*, Vol. 108, pp. 636-643 (1994), Accarino, et al "Modification Of Small Bowel Mechanosensitivity By Intestinal Fat", *GUT*, Vol. 48, pp. 690-695 (2001); Accarino, et al, "Gut Perception In Humans Is Modulated By Interacting Gut Stimuli", *Am. J. Physiol. Gastrointestinal Liver Physiol.*, Vol. 282, pp. G220-G225 (2002) and Accarino, et al, "Attention And Distraction Colon Affects On Gut Perception", *Gastroenterology*, Vol. 113, pp. 415-442 (1997).

Figure 8:
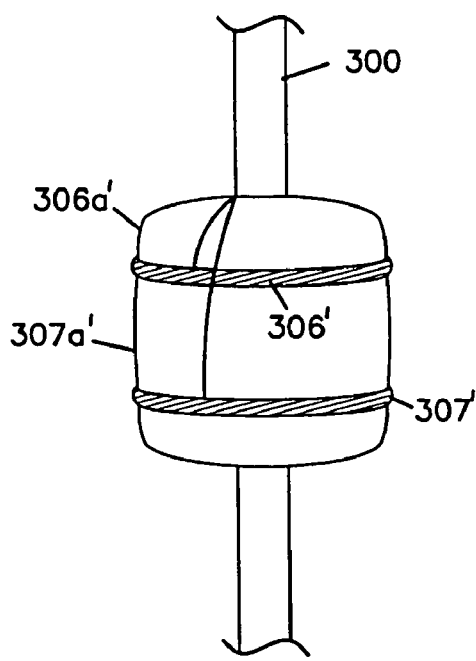
FIG. 8 is a side elevation view of a balloon portion of an apparatus for use in the embodiment of FIG. 7.
Figure 9:
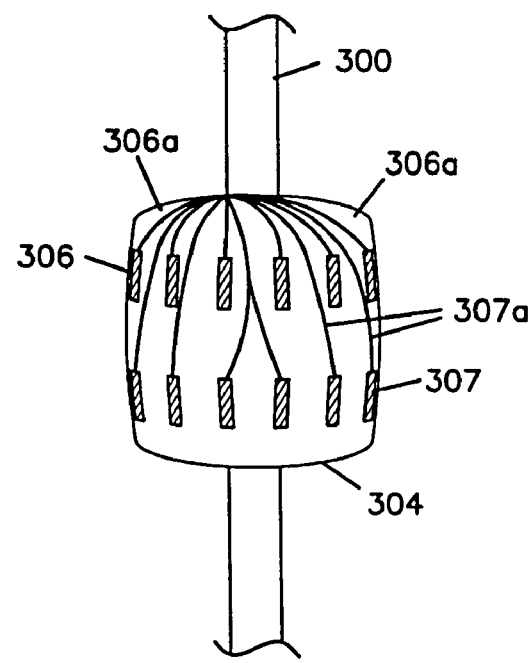
FIG. 9 is a side elevation view of an alternative embodiment of a balloon portion of an apparatus for use in the embodiment of FIG. 7.
Figure 10:
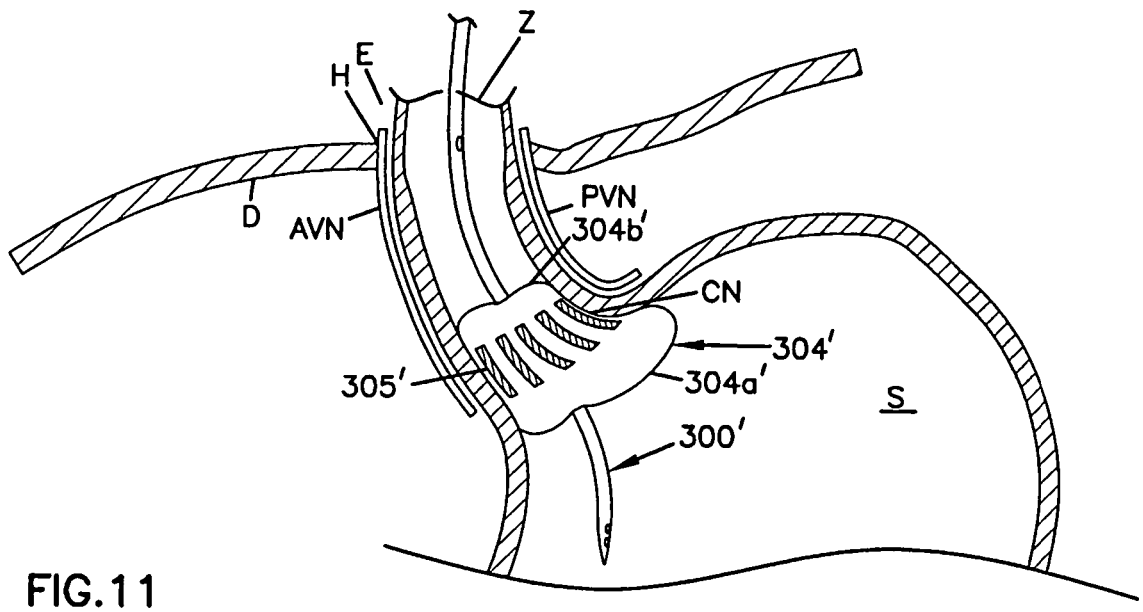
FIG. 10 is a side sectional view of a patients' stomach in illustrating a yet alternative embodiment of the apparatus of FIG. 7.

Alternative embodiments of the transmucosal stimulation device of FIG. 7 are shown in FIGS. 8 and 9. In FIG. 8, the balloon 304' is conical in shape with a base end 304a' placed distally on the tube 300'. After expansion, the base end 304a' expands within the stomach S. The physician then pulls on the tube 300'. The base end 304a' (which is larger in diameter than the esophagus E) abuts the stomach S at the cardiac notch CN acting as a stop. This insures the electrodes 305' (only a single array is shown for ease of illustration) abuts the mucosal tissue at the junction of the stomach S and esophagus E. The electrodes 305' are on the narrow end 304b' of the balloon 304' and expansion of the balloon 304' ensures contact of the electrodes with the mucosal tissue.

FIG. 9 illustrates an embodiment using two balloons 304" and 309". The distal balloon 309", when expanded, is larger than the esophagus E and acts as a stop when the physician pulls on the tube 300". The electrodes 305" are on a smaller balloon 304" which may expand in the esophagus E. The balloon 304", 309" are positioned for the electrodes 305" to be against the mucosal tissue at the junction of the stomach S and esophagus E when the distal balloon 309" abuts the cardiac notch CN and the proximal balloon 304" is expanded. The electrodes may be positioned to be completely within the stomach to reduce risk of injury to esophageal tissue. More conveniently, a tube such as the afore-mentioned Bards tube may be modified for electrodes to be placed on the proximal side of the gastric balloon.

In all of the foregoing, a balloon is expanded to urge the electrodes against the mucosal tissue. While this is a presently preferred embodiment, any mechanism for urging the electrodes against the mucosal tissue may be used. In each of FIGS. 8 and 9, the tube 300', 300" is shown as it passes through the balloons 304', 304" and 309". This illustration is made to indicate the tube passes through the balloons and does terminate at the balloons. In fact, as the tube 300', 300" passes through the balloons 304', 304" and 309" it would be surrounded by the material of the balloons 304', 304" and 309" and would not be visible.

Figure 12:
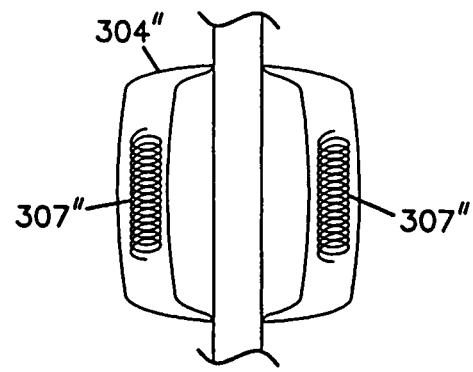
FIG. 12 is a schematic view of a balloon with magnetic coils.

A still further embodiment is shown in FIG. 12. Instead of directly stimulating with current, the nerves are stimulated with magnetic fields. In this case, the electrodes are coils 307''' insulated within the balloon 304'''. The coils 307''' create magnetic fields which inductively couple with the vagus nerves to create the blocking and stimulating impulses within the nerves.

While FIGS. 7-12 show electrodes on a balloon, electrodes can be placed on a catheter which resides in the esophagus. For example, CardioCommand, Inc., Tampa, Fla., USA markets a product TapScope™ and other related products which include a catheter having ring electrodes spaced apart along the length of the catheter near a distal tip of the catheter. The esophagus is a so-called "potential space" in that when empty of contents, the catheter collapses. With a catheter in the esophagus, the esophagus collapses onto the catheter with the esophagus wall in contact with the electrodes.

The TapScope (which comes in various sizes—e.g., 5, 10 or 18 French) is used positioned high in the esophagus with the electrodes placed near the heart. The TapScope is stimulated to cause pacing of the heart. Such pacing is using to perform cardiac stress testing patients. It is particularly useful in patients who are not ambulatory or who cannot tolerate more traditional stress testing (such as dobutamine stress testing. A discussion of such use of the TapScope can be found in Lee, et al., "Nonexercise Stress Transthoracic Echocardiography: Transesophageal Atrial Pacing Versus Dobutamine Stress", *J. Amer College of Cardiology*, Vol. 33, No. 2 pp. 506-511 (1999).

The TapScope can be modified to lengthen the catheter to position electrodes near or below the diaphragm to apply a blocking signal instead of a stimulating signal. The TapScope can also be modified to provide a hollow center to permit concurrent use of the TapScope as a gastric or jejunal tube. Further, the device can be modified to place an inflatable balloon on the catheter to reside in the stomach. The inflated balloon acts as a stop to prevent withdrawing the catheter prematurely and insure accurate positioning of the electrodes near or below the diaphragm.

ii. Application to Acute Pancreatitis

When energized with a blocking frequency, the embodiment of FIG. 7 is useful for treating acute or recurrent pancreatitis. This extremely serious disease is characterized by an over-active pancreas which excretes digestive enzymes to such an extent that the pancreas itself is digested. The disease can be extremely painful. In many cases, the disease is fatal. The number of US patients who suffer an episode of acute pancreatitis is approximately 185,000 annually. Baron, et al., "Acute Necrotizing Pancreatitis", *New England J. of Medicine*, Vol. 340, No. 18, pp. 1412-1417 (1999). This high incidence, coupled with the cost and length of stay required, make the total cost of this disease to society enormous. No definitive therapy is currently available to treat these patients except supportive care. Furthermore, the overall mortality rate for severe pancreatitis is about 20 to 30%. Id.

A recent study reported that the average total hospital cost to obtain a survivor of severe, acute pancreatitis is nearly $130,000 with an average length of hospital stay of 40 days. Soran, et al., "Outcome and quality of life of patients with acute pancreatitis requiring intensive care", *J. Sure. Res.*, 91(1), pp. 89-94 (2000). Further complicating the management of these patients is the uncertainty surrounding the prognosis because the course of the disease is unpredictable at initial presentation. Chatzicostas, et al., "Balthazar computed tomography severity index is superior to Ranson criteria and APACHE II and II scoring systems in predicting acute pancreatitis outcome", *J. Clinical Gastroenterology*, 36(3), pp. 253-260 (2003). If patients could be successfully treated during the initial phases of the disease, with a higher survival rate, there is a high probability of returning to a productive life. Soran, et al., supra.

Pancreatitis may be associated with a number of etiologies including chronic alcoholism or gallstones (e.g., gallstones lodged in the pancreatic or common duct). When acute pancreatitis becomes severe, treatment options are severely limited. Morbidity and mortality rates for pancreatitis are sobering. Baron, et al., "Acute Necrotizing Pancreatitis", *New England J. of Medicine*, Vol. 340, No. 18, pp. 1412-1417 (1999) and Steer et al., "Chronic Pancreatitis", *New England J. of Medicine*, pp. 1482-1490 (1995).

Down-regulating vagal activity can be used to treat pancreatitis. A recently reported finding in experimental pancreatitis demonstrated that the vagus nerves are strongly implicated in the pathophysiology of pancreatitis. Yoshinaga, et al., "Cholecystokinin Acts as an Essential Factor in the Exacerbation of Pancreatic Bile Duct Ligation-Induced Rat Pancreatitis Model Under Non-Fasting Condition", *Japanese J. Pharmacol*, Vol. 84, pp. 44-50 (2000). Pharmacologic means of decreasing pancreatic secretion have been attempted with limited success because of the dose-limiting side effects encountered with the drugs, their lack of specificity or their lack of availability. In fact, one recent trial of a specific blocker of parasympathetic (vagus nerves) control of secretion demonstrated a shortened recovery period in patients with acute pancreatitis while trials with other pancreatic down-regulating drugs that are less specific or potent have proven to be disappointing. Zapater, et al., "Do Muscarinic Receptors Play a Role in Acute Pancreatitis?", *Clin. Drug Invest.*, 20(6), pp. 401-408 (2000); Norton, et al., "Optimizing Outcomes in Acute Pancreatitis", *Drugs*, 61(11), pp. 1581-1591 (2001). Atropine is a drug that blocks parasympathetic nerve endings. It is known to be desirable to use atropine in acute pancreatitis patients to down-regulate pancreatic activity. Unfortunately, for most such patients, this drug cannot be used due to its many side effects.

Acute pancreatitis patients may be placed on intravenous feeding with the device 300 left in place for a chronic length of time (e.g., several days or weeks). At least the electrodes of the lower array 307 may be energized with a blocking signal for the treatment of acute pancreatitis. The invention permits down-regulation of pancreatic output through vagal blocking without the need for undesirable surgery for direct vagal access.

In addition to utility for treating pancreatitis, the present invention may be used to avoid pancreatitis in patients having an increased likelihood of developing the disease. For example, patients undergoing endoscopic retrograde cholangiopancreatography (ERCP) and/or related procedures are known to having a higher likelihood of developing pancreatitis. Such patients may be treated with the present invention with a blocking signal to down-regulate pancreatic output and reduce the likelihood of developing pancreatitis.

Many physicians treating patients with pancreatitis use a nasogastric tube as part of the treatment. As a result, the present invention is illustrated as being incorporated on a nasogastric tube. However, a significant body of physicians adheres to a belief that pancreatitis patients benefit from a feeding involving placing nourishment directly into the jejunum portion of the small intestine via a nasojejunal tube. While the present invention is illustrated in an embodiment with placement of the balloon and electrodes on a naso-gastric tube, the invention can also be placed on a nasojejunal tube or a nasogastricjejunal tube.

Improvements to Control Nerve Down-Regulation

While simulating a vagotomy through a nerve block as described above is beneficial, a complete and continuous block can have adverse consequences in some patients. The vagus nerve serves a wide variety of functions. For example, vagal activity contributes to pyloric relaxation (thereby promoting gastric emptying) as well as intestinal motility. Also, a vagotomized patient may experience a loss of the benefits of a vagotomy over time. For example, over time, the enteric nervous system may compensate for a vagotomy. Therefore, in patients who have experienced weight loss from vagotomy, some patients may experience a relapse of weight gain over time as the enteric nervous system compensates for the loss of vagal activity. As a result, a complete and permanent simulation of a vagotomy at times may be undesirable.

Animal studies performed by applicants reveal nerve and organ function recovery after cessation of a vagal blocking signal. In such studies pancreatic exocrine secretion is collected and measured in juvenile pigs. The collection of such secretions as a measure of vagal activity is described in Holst, et al., "Nervous control of pancreatic exocrine secretion in pigs", Acta Physiol. Scand. 105: 33-51 (1979) (in which an up-regulating stimulation of the vagus was studied).

Electrodes applied to both anterior and posterior vagal trunks are energized with a blocking signal. The signal is applied for a limited time (e.g., 5 minutes). In response to vagal blocking, pancreatic exocrine secretion drops significantly (e.g., by up to about 90% from baseline). After cessation of blocking, the level of pancreatic exocrine secretion gradually increases toward baseline. The speed of vagal activity recovery varies from subject to subject. However, 20 minutes is a reasonable example of the time needed to recover to baseline. After recovery, application of a blocking signal again down-regulates vagal activity which can then recover after cessation of the signal. Renewed application of the signal can be applied before full recovery. For example, after a limited time period (e.g., 10 minutes) blocking can be renewed resulting in average vagal activity not exceeding a level significantly reduced when compared to baseline.

Recognition of recovery of vagal activity (and recognition of the significant variability between subjects) permits a treatment therapy and apparatus with enhanced control and enhanced treatment options. FIG. 14 illustrates vagal activity over time in response to application of a blocking signal as described above and further illustrates recovery of vagal activity following cessation of the blocking signal. It will be appreciated that the graph of FIG. 14 is illustrative only. It is expected there will be significant patient-to-patient variability. For example, some patients' responses to a blocking signal may not be as dramatic as illustrated. Others may experience recovery slopes steeper or shallower than illustrated. Also, vagal activity in some subjects may remain flat at a reduced level before increasing toward baseline activity. However, based on the afore-mentioned animal experiments, FIG. 14 is believed to be a fair presentation of a physiologic response to blocking.

In FIG. 14, vagal activity is illustrated as a percent of baseline (i.e., vagal activity without the treatment of the present invention). Vagal activity can be measured in any number of ways. For example, quantities of pancreatic exocrine secretion produced per unit time is an indirect measurement of such activity. Also, activity can be measured directly by monitoring electrodes on or near the vagus. Such activity can also be ascertained qualitatively (e.g., by a patient's sensation of bloated feelings or normalcy of gastrointestinal motility).

In FIG. 14, the vertical axis is a hypothetical patient's vagal activity as a percent of the patient's baseline activity (which varies from patient to patient). The horizontal axis represents the passage of time and presents illustrative intervals when the patient is either receiving a blocking signal as described or the blocking signal is turned off (labeled "No Blocking").

As shown in FIG. 14, during a short period of receiving the blocking signal, the vagal activity drops dramatically (in the example shown, to about 10% of baseline activity). After cessation of the blocking signal, the vagal activity begins to rise toward baseline (the slope of the rise will vary from patient to patient). The vagal activity can be permitted to return to baseline or, as illustrated in FIG. 14, the blocking signal can be re-instituted when the vagal activity is still reduced. In FIG. 14, the blocking signal begins when the vagal activity increases to about 50% of baseline. As a consequence, the average vagal activity is reduced to about 30% of the baseline activity. It will be appreciated that by varying the blocking time duration and the "no blocking" time duration, the average vagal activity can be greatly varied.

The flexibility to vary average vagal activity gives an attending physician great latitude in treating a patient. For example, in treating obesity, the blocking signal can be applied with a short "no blocking" time to reduce weight as rapidly as possible. If the patient experiences discomfort due to dysmotility, the duration of the "no blocking" period can be increased to improve patient comfort. Also, the reduction of enzyme production can result in decreased fat absorption with consequential increase of fat in feces. The blocking and no blocking duration can be adjusted to achieve tolerable stool (e.g., avoiding excessive fatty diarrhea).

The control afforded by the present invention can be used to prevent the enteric nervous system's assumption of control since vagal activity is not completely interrupted as in the case of a surgical and permanent vagotomy. Further, pancreatic production of digestive enzymes (such as the fat digesting enzyme lipase) is not eliminated but is controllably reduced.

While patient weight loss and comfort may be adequate as feedback for determining the proper parameters for duration of blocking and no blocking, more objective tests can be developed. For example, the duration of blocking and no blocking can be adjusted to achieve desired levels of enzyme production and nutrient digestion. In one example of drug therapy for obesity, orlistat blocks the action of lipase. Lipase is a fat-digesting enzyme. As a consequence of this reduction in lipase, the fat content of feces increases. It is generally regarded as desirable to modulate drug intake so that fecal fat does not exceed 30% of ingested fat. Similarly, the blocking and no blocking durations can be modulated to achieve the same result. Such testing can be measured and applied on a per patient basis or performed on a statistical sampling of patients and applied to the general population of patients.

FIG. 13 illustrates an embodiment with even more objective means to modulating the block and no block durations. In FIG. 13, a sensing electrode SE is added to monitor vagal activity. While sensing electrode SE is shown as an additional electrode to blocking electrode-BE, it will be appreciated a single electrode could perform both functions. The sensing and blocking electrodes are connected to a controller 102'. Controller 102' is the same as controller 102 previously described with the additive function of receiving a signal from sensing electrode SE (which yields the actual vagal activity of the graph of FIG. 14). When the sensing electrode SE yields a signal representing a targeted maximum vagal activity or tone (e.g., 50% of baseline as shown in FIG. 14) the controller 102' energizes the blocking electrode BE with a blocking signal. As described with reference to controller 102, controller 102' can be remotely programmed as to parameters of blocking duration and no blocking duration as well as targets for initiating a blocking signal As shown above, the present invention uniquely uses a recovery of the vagus nerve to control a degree of down-regulation of vagal activity. This gives a physician enhanced abilities to control a patient's therapy for maximum therapeutic effectiveness with minimum patient discomfort.

With the foregoing detailed description of the present invention, it has been shown how the objects of the invention have been attained in a preferred manner. Modifications and equivalents of disclosed concepts such as those which might readily occur to one skilled in the art, are intended to be included in the scope of the claims which are appended hereto.

We claim:

1. A method for treating obesity comprising:
   positioning an electrode on a vagus nerve of an obese patient at a location below a vagal innervation of the heart, with the vagus nerve innervating at least one alimentary tract organ;
   treating the patient's obesity by applying an electrical treatment signal to the electrode with the electrical treatment signal having:
   a) a frequency selected for said signal to at least partially downregulate nerve impulses on said vagus nerve, wherein said signal has a frequency in excess of 200 Hz;
   b) a plurality of on-times separated by a plurality of off-times, said signal applied during said on-times and not applied during said off-times, wherein a duration of the off-times is selected to allow at least partial recovery of the activity of said vagus nerve, and wherein the on and off times of the electrical signal treatment reduce pancreatic and biliary output via inhibition of pancreo-biliary output of the obese patient; and
   wherein the electrical signal treatment is applied without simultaneously applying a neural impulse-inducing secondary electrical signal to the vagus nerve on a proximal side of said location.

2. A method according to claim 1 wherein application of said electrical signal is variable by a controller to alter a characteristic of said electrical treatment signal.

3. A method according to claim 2 wherein said electrical treatment signal is regulated to heighten a sensation of satiety of said patient.

4. A method according to claim 1 wherein a duration of said off time is selected to avoid excessive fecal fat in a stool of said patient.

5. A method according to claim 1 wherein said frequency is selected to block afferent signals on the vagus nerve.

6. A method according to claim 1 wherein said frequency is selected to block efferent signals on the vagus nerve.

7. A method according to claim 1 wherein said frequency is selected to block both afferent and efferent signals on the vagus nerve.

8. A method according to claim 1 wherein said frequency is selected to block myelinated fibers of the vagus nerve.

9. A method according to claim 1 wherein said frequency is selected to block unmyelinated fibers of the vagus nerve.

10. A method according to claim 1 wherein said frequency is selected to block both myelinated and unmyelinated fibers of the vagus nerve.

11. A method according to claim 1 wherein the electrical treatment signal is applied to a vagal trunk.

12. A method according to claim 1 wherein the electrical treatment signal is applied to a vagal branch.

13. A method according to claim 1 wherein the electrical treatment signal is applied to both an anterior vagus nerve and a posterior vagus nerve of the patient.

14. A method according to claim 1 wherein the electrical treatment signal is applied to a selected one of an anterior vagus nerve and a posterior vagus nerve of the patient.

15. A method according to claim 1 wherein the electrical treatment signal is applied to the vagus nerve at a location near or distal to a diaphragm of the patient.

16. A method according to claim 1 further comprising monitoring a vagal activity of said patient.

17. A method according to claim 16, wherein said monitoring includes monitoring a discomfort of said patient.

18. A method according to claim 16, wherein said monitoring includes monitoring a fecal fat content of said patient.

19. A method according to claim 16, wherein said monitoring includes electrically monitoring a neural activity of said patient.

20. A method according to claim 1 wherein said frequency is at least 500 Hz.

21. A method according to claim 1, wherein said on time and said off time is varied to obtain an average vagal activity of at least 30%.

22. A method according to claim 1, wherein said on time is about two to five minutes.

23. A method according to claim 1, wherein said off time is selected to increase weight loss.

24. A method according to claim 1, wherein said off time is selected to increase patient comfort.

* * * * *